US008909351B2

(12) United States Patent
Dinsmoor et al.

(10) Patent No.: US 8,909,351 B2
(45) Date of Patent: Dec. 9, 2014

(54) IMPLANTABLE MEDICAL DEVICES AND SYSTEMS HAVING DUAL FREQUENCY INDUCTIVE TELEMETRY AND RECHARGE

(75) Inventors: David A. Dinsmoor, St. Paul, MN (US); Joel A. Anderson, Brooklyn Park, MN (US); Timothy Denison, Minneapolis, MN (US); John J. Grevious, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 343 days.

(21) Appl. No.: 13/019,568

(22) Filed: Feb. 2, 2011

(65) Prior Publication Data
US 2011/0190852 A1    Aug. 4, 2011

Related U.S. Application Data

(60) Provisional application No. 61/301,185, filed on Feb. 3, 2010.

(51) Int. Cl.
*A61N 1/00* (2006.01)
*A61N 1/372* (2006.01)
*A61N 1/378* (2006.01)
*A61B 5/00* (2006.01)

(52) U.S. Cl.
CPC .......... *A61N 1/37223* (2013.01); *A61N 1/3787* (2013.01); *A61N 1/37229* (2013.01); *A61B 5/0031* (2013.01)
USPC .............................................. 607/60; 607/61

(58) Field of Classification Search
CPC ............. A61N 1/3787; A61N 1/37223; A61B 5/0031; H03H 7/40; H02J 5/05; H01F 38/14
USPC ........................... 607/30, 32, 60, 61; 128/903
See application file for complete search history.

(56) References Cited

U.S. PATENT DOCUMENTS

| 3,229,684 | A | 1/1966 | Nagumo et al. |
| 3,758,865 | A | 9/1973 | McKibben |
| 3,796,221 | A | 3/1974 | Hagfors |
| 4,166,470 | A | 9/1979 | Neumann |

(Continued)

FOREIGN PATENT DOCUMENTS

| GB | 1492990 | 11/1977 |
| WO | 94/28560 | 9/1994 |
| WO | 2009/056167 | 7/2009 |

OTHER PUBLICATIONS

"An Implantable Bionic Network of Injectable Neural Prosthetic Devices: The Future Platform for Functional Electrical Stimulation and Sensing to Restore Movement and Sensation", Library of Congress, BioMedical Engineer Fundamentals, p. 34-1-p. 34-18.

(Continued)

*Primary Examiner* — Catherine Voorhees
(74) *Attorney, Agent, or Firm* — Withers & Keys, LLC

(57) ABSTRACT

Implantable devices and related systems utilize coils or coil portions of a coil for inductive telemetry at one frequency and recharge at another frequency. The coils or coil portions are included in one or more tank circuits that share at least one node between the coils or coil portions. The recharge application may be provided with variations for aspects including power management and rectification. The telemetry application may be provided with variations for aspects including receiver connectivity for the downlink and coil driving for the uplink.

20 Claims, 31 Drawing Sheets

(56) References Cited

U.S. PATENT DOCUMENTS

| | | |
|---|---|---|
| 4,197,850 A | 4/1980 | Schulman et al. |
| 4,345,604 A | 8/1982 | Renirie |
| 4,679,560 A | 7/1987 | Galbraith |
| 5,218,343 A | 6/1993 | Stobbe |
| 5,235,980 A | 8/1993 | Varrichio |
| 5,260,701 A | 11/1993 | Guern |
| 5,279,292 A | 1/1994 | Baumann |
| 5,314,457 A | 5/1994 | Jeutter |
| 5,324,315 A | 6/1994 | Grevious |
| 5,324,316 A | 6/1994 | Schulman et al. |
| 5,405,367 A | 4/1995 | Schulman et al. |
| 5,522,865 A | 6/1996 | Schulman et al. |
| 5,569,307 A | 10/1996 | Schulman |
| 5,630,836 A | 5/1997 | Prem et al. |
| 5,658,319 A | 8/1997 | Kroll |
| 5,674,264 A | 10/1997 | Carter et al. |
| 5,680,134 A | 10/1997 | Tsui |
| 5,702,431 A | 12/1997 | Wang |
| 5,713,939 A | 2/1998 | Nedungadi et al. |
| 5,733,313 A | 3/1998 | Barreras, Sr. et al. |
| 5,741,316 A | 4/1998 | Chen et al. |
| 5,755,748 A | 5/1998 | Borza |
| 5,769,877 A | 6/1998 | Barreras, Sr. |
| 5,807,397 A | 9/1998 | Barreras |
| 5,814,089 A | 9/1998 | Stokes et al. |
| 5,991,664 A | 11/1999 | Seligman |
| 5,995,874 A | 11/1999 | Borza |
| 5,999,857 A | 12/1999 | Weijand |
| 6,011,964 A | 1/2000 | Saitoh |
| 6,047,214 A | 4/2000 | Mueller |
| 6,185,460 B1 | 2/2001 | Thompson |
| 6,308,101 B1 | 10/2001 | Faltys |
| 6,321,067 B1 | 11/2001 | Suga |
| 6,442,434 B1 | 8/2002 | Zarinetchi |
| 6,456,883 B1 | 9/2002 | Torgerson |
| 6,477,425 B1 | 11/2002 | Nowick |
| 6,516,227 B1 | 2/2003 | Meadows et al. |
| 6,549,807 B1 | 4/2003 | Kroll |
| 6,631,296 B1 | 10/2003 | Parramon et al. |
| 6,701,188 B2 | 3/2004 | Stroebel |
| 6,772,011 B2 | 8/2004 | Dolgin |
| 6,856,838 B2 | 2/2005 | Parramon et al. |
| 7,015,769 B2 | 3/2006 | Schulman |
| 7,079,901 B1 | 7/2006 | Loftin et al. |
| 7,107,103 B2 | 9/2006 | Schulman |
| 7,167,756 B1 | 1/2007 | Torgerson et al. |
| 7,177,691 B2 | 2/2007 | Meadows |
| 7,177,698 B2 | 2/2007 | Klosterman et al. |
| 7,191,007 B2 | 3/2007 | Desai |
| 7,209,792 B1 | 4/2007 | Parramon et al. |
| 7,226,442 B2 | 6/2007 | Sheppard, Jr. |
| 7,379,774 B2 | 5/2008 | Gord |
| 7,379,775 B2 | 5/2008 | Parramon et al. |
| 7,428,438 B2 | 9/2008 | Parramon et al. |
| 7,437,193 B2 | 10/2008 | Parramon et al. |
| 7,486,048 B2 | 2/2009 | Tsukamoto |
| 7,515,012 B2 | 4/2009 | Schulman |
| 7,555,345 B2 | 6/2009 | Wahlstrand et al. |
| 7,587,246 B2 | 9/2009 | Hochmair |
| 7,657,320 B2 | 2/2010 | Chadwick |
| 7,780,613 B2 | 8/2010 | Sherman |
| 7,912,551 B2 * | 3/2011 | Wosmek et al. ............... 607/60 |
| 7,917,226 B2 | 3/2011 | Nghiem |
| 7,957,804 B2 | 6/2011 | Abreu |
| 2002/0177884 A1 | 11/2002 | Ahn et al. |
| 2002/0188333 A1 | 12/2002 | Nowick |
| 2004/0068298 A1 | 4/2004 | Parramon et al. |
| 2005/0075693 A1* | 4/2005 | Toy et al. .................. 607/60 |
| 2005/0075697 A1 | 4/2005 | Olson |
| 2005/0119716 A1 | 6/2005 | McClure |
| 2005/0131495 A1 | 6/2005 | Parramon |
| 2005/0288739 A1 | 12/2005 | Hassler et al. |
| 2006/0020306 A1 | 1/2006 | Davis et al. |
| 2007/0060967 A1 | 3/2007 | Strother et al. |
| 2008/0027513 A1 | 1/2008 | Carbunaru |
| 2008/0039903 A1 | 2/2008 | Chadwick |
| 2008/0051854 A1 | 2/2008 | Bulkes |
| 2008/0172109 A1 | 7/2008 | Rahman et al. |
| 2009/0018618 A1 | 1/2009 | Parramon et al. |
| 2009/0118796 A1 | 5/2009 | Chen et al. |
| 2009/0216296 A1 | 8/2009 | Meskens |
| 2009/0281597 A1 | 11/2009 | Parramon et al. |
| 2010/0069992 A1 | 3/2010 | Aghassian |
| 2010/0141042 A1* | 6/2010 | Kesler et al. .................. 307/104 |
| 2010/0179618 A1 | 7/2010 | Marnfeldt |
| 2010/0204756 A1 | 8/2010 | Aghassian |
| 2010/0219796 A1 | 9/2010 | Kallmyer |
| 2010/0328077 A1 | 12/2010 | Stein |
| 2010/0331920 A1* | 12/2010 | DiGiore et al. ............... 607/61 |
| 2011/0112610 A1 | 5/2011 | Rahman et al. |
| 2011/0112611 A1 | 5/2011 | Aghassian |

OTHER PUBLICATIONS

Tang et al., "Data Transmission from an Implantable Biotelemeter by Load-Shift Keying, Using Circuit Configuration Modulation", IEEE Transactions BioMedical Engineer, vol. 5, May 5, 1993, pp. 524-528.
Zierhofer, "A Class E Tuned Power Oscillator for Inductive Transmission of Digital Data & Power", IEEE Transactions BioMedical Engineer, 1991, pp. 782-792.
U.S. Appl. No. 12/699,830, filed Feb. 3, 2010.
U.S. Appl. No. 13/096,073, filed Apr. 28, 2011.
PCT/US2011/023463 International Search Report mailed May 6, 2011.
U.S. Appl. No. 12/699,830 Office Action dated Aug. 21, 2012.
U.S. Appl. No. 12/699,830 Response filed Nov. 20, 2012.
Majerus et al., "Telemetry Platform for Deeply Implanted Biomedical Sensors", IEEE Xplore, pp. 1-6.
U.S. Appl. No. 12/699,830 Final Office Action dated Jan. 28, 2013.
U.S. Appl. No. 12/699,830 After Final Response filed Mar. 28, 2013.
U.S. Appl. No. 12/699,830 Advisory Action mailed Apr. 2, 2013.
U.S. Appl. No. 12/699,830 RCE-Response filed Apr. 26, 2013.

* cited by examiner

IMPLANTABLE MEDICAL DEVICES AND SYSTEMS HAVING DUAL FREQUENCY INDUCTIVE TELEMETRY AND RECHARGE

RELATED APPLICATIONS

The present application claims priority to U.S. Provisional Application No. 61/301,185, filed on Feb. 3, 2010, and entitled IMPLANTABLE MEDICAL DEVICES AND SYSTEMS HAVING DUAL FREQUENCY INDUCTIVE TELEMETRY AND RECHARGE, which is incorporated by reference herein.

TECHNICAL FIELD

Embodiments relate to implantable medical devices that utilize inductive couplings for telemetry at one frequency and for recharge at another frequency. More particularly, embodiments relate to implantable medical devices that use a dedicated coil or a dedicated portion of a shared coil for the telemetry and recharge applications.

BACKGROUND

Implantable medical devices (IMD) may provide a variety of different therapies and other functions including stimulation, drug infusion, physiological sensing, and the like. The IMDs receive programming from an external device and may also share information that has been collected with the external device. Many IMDs communicate with the external device using an inductive form of telemetry where a telemetry head is held in communication range of the IMD so that inductive signals may be exchanged.

The inductive downlink is obtained by a coil within the IMD that is tuned to a telemetry frequency, e.g., 175 kilohertz, being emitted by a coil within the external device. Likewise, the inductive uplink is provided by a coil within the IMD that is tuned to emit signals at a telemetry frequency of the coil of the external device. The uplink and downlink telemetry frequencies are frequently the same and a single coil in each device is tuned to a single frequency that is used for both the uplink and the downlink.

Many IMDs operate on battery power and therefore have a limited lifetime of operation before a replacement or a recharge is necessary. For IMDs with a rechargeable power source, the recharge energy may be received via inductive coupling. The external device has a coil tuned to a recharge frequency, e.g., 5 kilohertz, which may differ from the telemetry frequency. Many commercially available IMDs have a second coil that is tuned to the recharge frequency being emitted by the external device. However, the circuitry utilizing the first and second coils may be distinct circuits that may share only power and ground connections, may require more pads and ultimately more space on a circuit board, and so forth.

Furthermore, while using two coils of distinct circuits within the IMD adequately establishes telemetry and recharge applications, the size occupied by two separate coils of distinct circuits restricts the ability to make smaller IMDs. Thus, miniaturized IMD designs may call for a reduction in the space being occupied by the two coils. In some cases the miniaturized designs may call for a single coil such that the inclusion of the telemetry application of one circuit having a telemetry coil precludes inclusion of the recharge application of a distinct circuit having a recharge coil.

SUMMARY

Embodiments address issues such as these and others by providing IMDs that may include coils or coil portions used for telemetry and recharge applications of differing frequencies. The embodiments include one or more tank circuits that share one or more nodes in addition to power and ground where each includes a dedicated coil or a dedicated portion of a coil being shared and where a tank circuit including a coil or dedicated coil portion becomes active for a corresponding function such as telemetry or recharge by activation of switches. The tank circuit(s) is/are tuned to an appropriate frequency based in part on the inclusion of the dedicated coil or dedicated portion of a shared coil.

DETAILED DESCRIPTION

Embodiments provide for medical systems including IMDs that offer both inductive telemetry and recharge applications at different frequencies. The telemetry may include uplink, downlink, or both, and various configurations for the telemetry may be provided. Likewise, various configurations may be provided for the recharge application, including various rectifier configurations and in some cases power management approaches.

Figure 1:
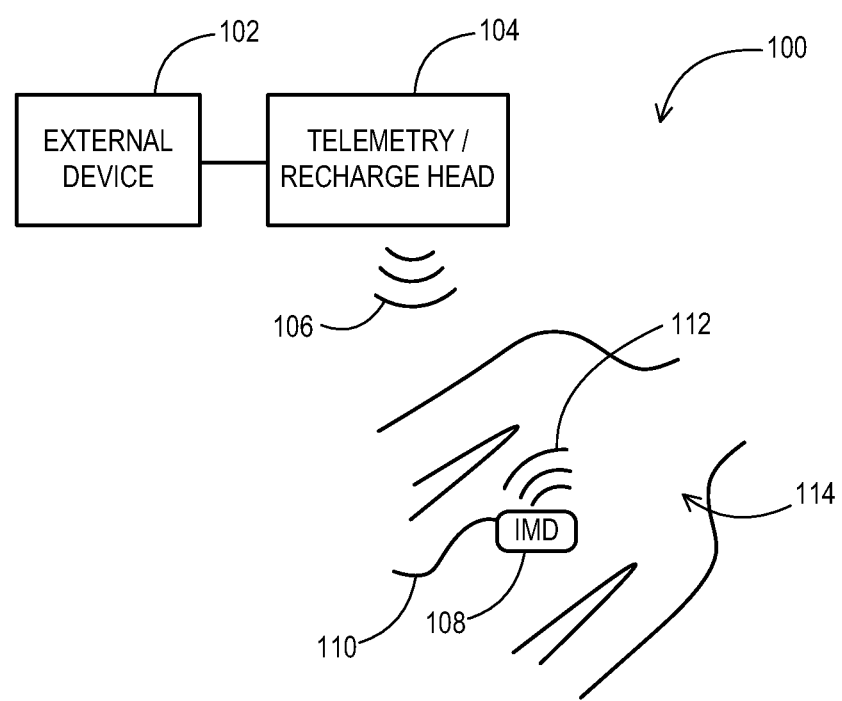
FIG. 1 shows a typical operating environment for a medical system including an external device and an IMD according to various embodiments.

FIG. 1 shows a typical operating environment for a medical system 100 that includes an external device 102 and an IMD 108. The external device 102 may provide programming and data collection services by using inductive telemetry. The external device 102 may also provide recharge services by using an inductive coupling. A telemetry/recharge head 104 that is tethered to the external device 102 may be placed nearby the patient's body 114 and in communication range of the IMD 108 so that an inductive coupling occurs between a coil within the head 104 and the coil within the IMD 108.

The head 104 may emit inductive signals 106 that represent downlink telemetry signals or recharge signals. The telemetry signals are emitted at one frequency while the recharge signals are emitted at a different time and at another frequency. For instance, the telemetry signals may be 175 kilohertz while the recharge signals are at 5 kilohertz. However, many different frequencies are possible for both telemetry and recharge and the recharge frequency may either be of a higher or lower frequency than the telemetry. While a single external device 102 is shown for both telemetry and recharge applications, it will be appreciated that these applications may be provided by different external devices where a first external device conducts a telemetry session at the telemetry frequency and a second external device conducts a recharge session at the recharge frequency at some other time.

Embodiments of the IMD 108 may utilize the same coil for the downlink and for the recharge but using separate portions of the coil while in other cases separate coils may be used. In such embodiments, the IMD 108 receives the inductive signals 106, including both the telemetry and the recharge signals, on the one or more coils. Embodiments of the IMD 108 may additionally or alternatively utilize the same one or more coils for the uplink and for the recharge. In such embodiments, the IMD 108 emits inductive telemetry signals 112 from the telemetry coil or coil portion, and those signals are received by the coil of the head 104.

The IMD 108 of this example includes an extension 110 such as a medical lead or a catheter that allows the IMD 108 to perform one or more medical functions. For instance, where the extension 110 is a medical lead, then IMD 108 may provide stimulation signals to the body 114 via electrodes on the lead and/or may sense physiological signals of the body 114 via the electrodes. Where the extension 110 is a catheter, the IMD 108 may infuse drugs into the body 114. These medical functions may be performed by the IMD 108 in accordance with programming received via the inductive telemetry signals and may be performed by using battery power that is replenished by the inductive recharge signals.

Figure 2:
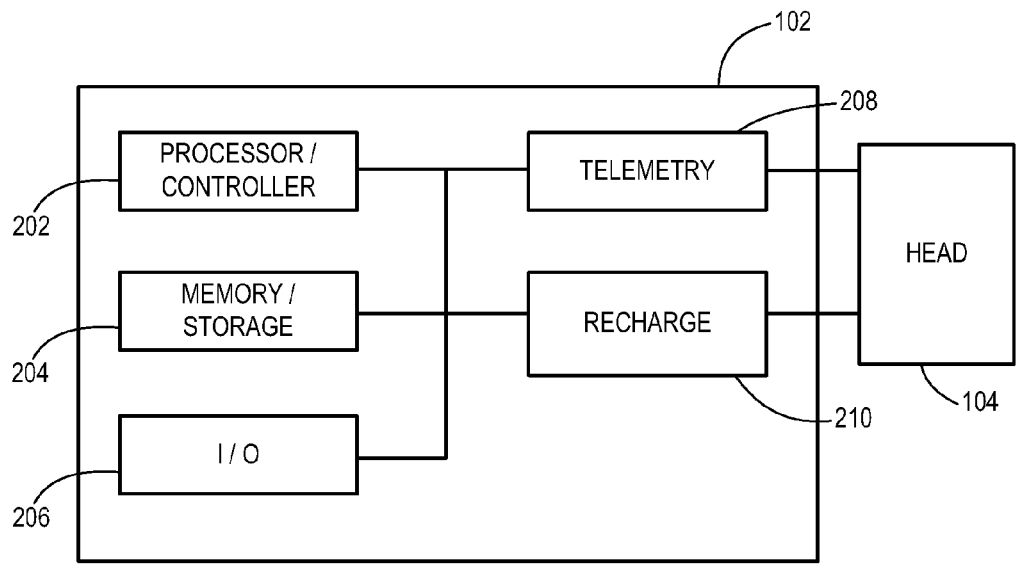
FIG. 2 shows a diagram of components of an example of an external device.

FIG. 2 shows components of one example of the external device 102. The external device 102 includes a processor/controller 202 and memory/storage device(s) 204. The external device 102 may also include local input/output (I/O) ports 206 such as to provide local screen displays and to receive user input via keyboard, mouse, and so forth. The external device 102 also includes a telemetry module 208 used to establish the telemetry to the IMD 108, and the telemetry module 208 may provide signals at the telemetry frequency to the head 104 during telemetry sessions. The external device of this example also includes a recharge module 210 used to transfer recharge energy to the IMD 108, and the recharge module 210 may provide signals at the recharge frequency to the head 104 during recharge sessions.

The memory/storage devices 204 may be used to store information in use by the processor 202. For instance, the memory/storage 204 may store therapy parameters that are input by a clinician or patient that are to be downlinked into the IMD 104. The memory/storage devices 204 may also store programming that is used by the processor 202 to control the telemetry and recharge actions of the external device 102. The memory/storage devices 204 may be of various types, such as volatile, non-volatile, or a combination of the two. The memory storage devices 204 may be used to store information for a long term and may be of various types such as electronic, magnetic, and optical drives. The memory/storage devices 204 are examples of computer readable media that may store information in the form of computer programming, data structures, and the like.

The processor/controller 202 includes logic to perform various operations to allow telemetry and/or recharge sessions with the IMD 108. The processor/controller 202 may be of various forms. For instance, the processor/controller 202 may include a general-purpose programmable processor that executes software that is stored on the memory/storage devices 204 or elsewhere. Other examples include a dedicated purpose hardware circuit or hard-wired digital logic. The processor/controller 202 may communicate with the various other components through one or more data buses.

Figure 3:
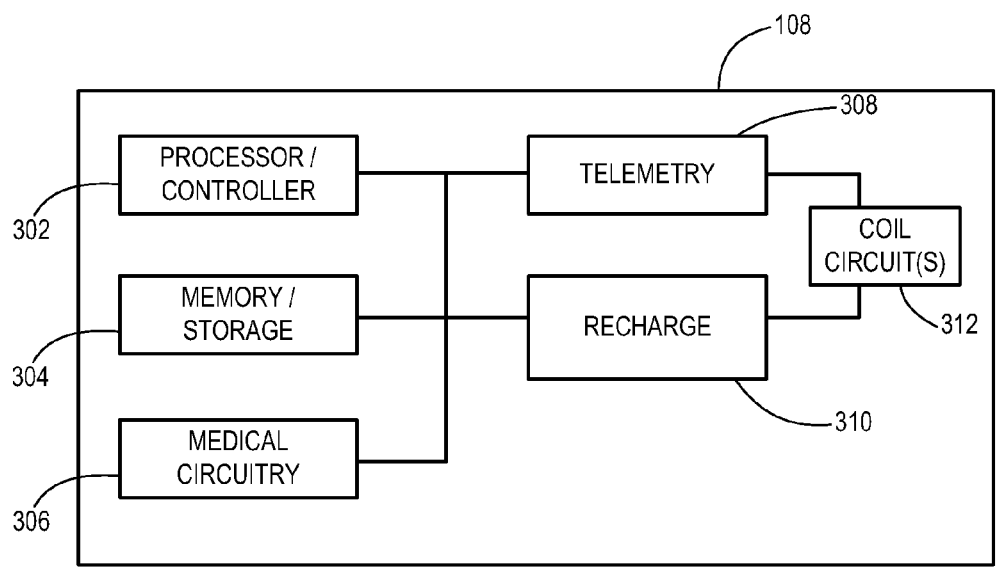
FIG. 3 shows a diagram of components of an example of an IMD.

FIG. 3 shows components of one example of the IMD 108. The IMD 108 includes a processor/controller 302 (also referred to in FIGS. 5-29, 32, and 33 as ©) and a memory/storage device(s) 304. The IMD 108 also includes medical circuitry 306 that performs a medical task such as stimulation, drug delivery, monitoring, and the like. The IMD 108 also includes telemetry circuitry 308 used to establish the uplink and/or downlink telemetry with the external device 102 in conjunction with single coil circuitry 312. The IMD 108 further includes recharge circuitry 310 used to receive recharge energy from the external device 102 in conjunction with the coil circuitry 312.

The memory/storage devices 304 may be used to store information in use by the processor/controller 302 such as programming and data values. The memory/storage devices 304 may store additional information including therapy parameters that are used to control the medical circuitry 306. The memory/storage devices 304 may be of various types such as volatile, non-volatile, or a combination of the two. The memory/storage devices 304 are also an example of computer readable media that may store information in the form of computer programming, data structures, and the like.

The processor/controller 302 includes logic to perform operations that allow telemetry and recharge sessions with the external device 102 to be established. The processor/controller 302 may be of various forms like those discussed above for the processor/controller 202 of the external device 102, such as a general purpose processor, an application specific circuit, hardwired digital logic, and the like. The processor/controller 302 may communicate with the various other components through one or more data buses. The processor/controller 302 may also control silicon based switches that are either integral to the processor/controller 302 or separate electronic devices to provide the telemetry, recharge, and power management functions while using the one or more coils. These switches and other circuit details are discussed in more detail below with reference to FIGS. 4-33.

Figure 4:
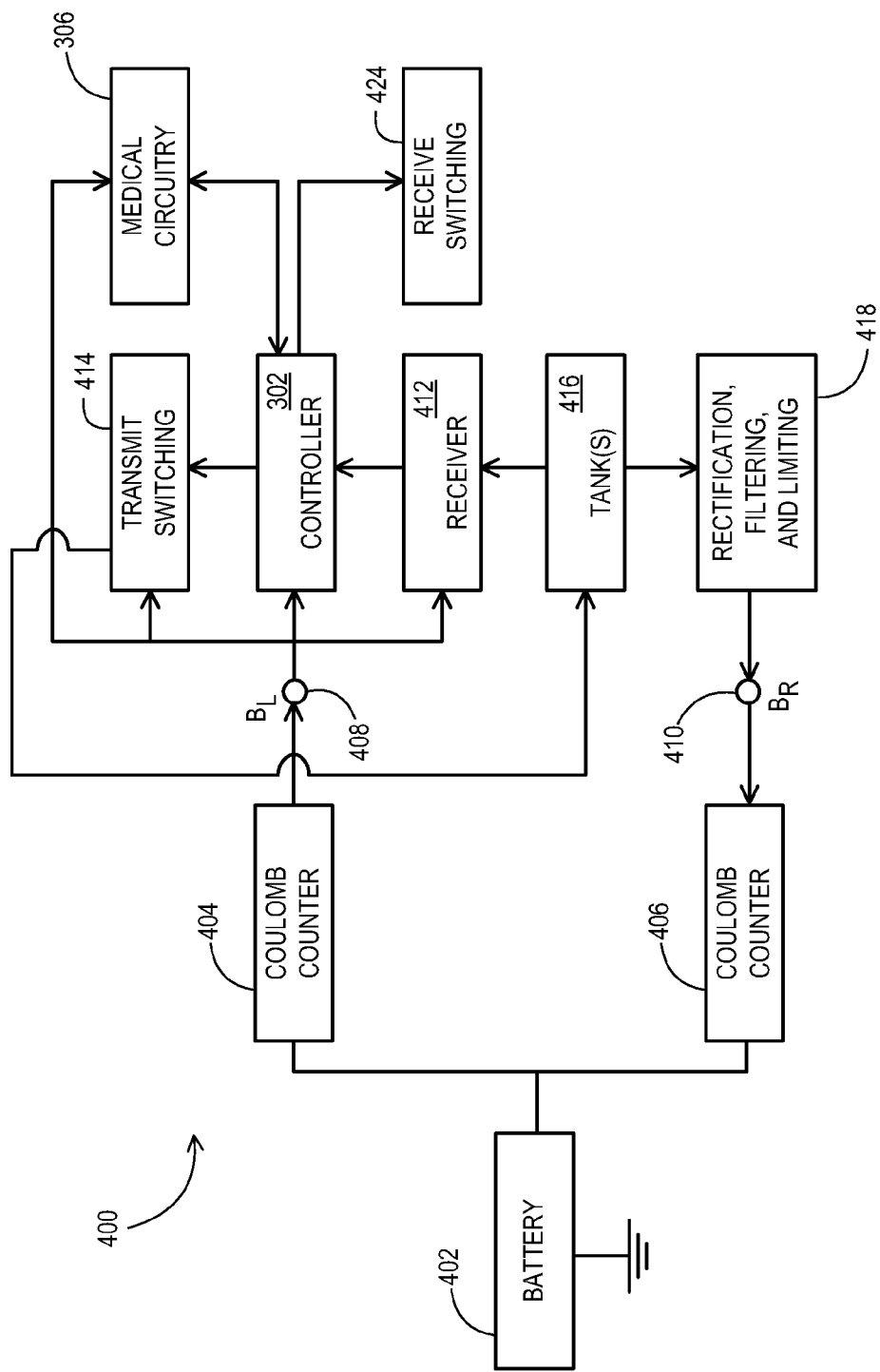
FIG. 4 shows a diagram of a load branch and a recharge branch of an example of an IMD.

FIG. 4 shows one example of a configuration 400 of circuit modules that may be employed in various embodiments of the IMD 108. This configuration 400 includes a battery 402 that provides the energy for the general operation of the IMD 108 including the operations being performed by the logic of the processor/controller 302 and the medical tasks being performed by the medical circuitry 306. The battery 402 also receives the energy being collected during the recharge session.

As shown, there is a load branch stemming from a node 408 (hereinafter $B_L$, as also shown in FIGS. 5-29, 32, and 33) and a recharge branch stemming from a node 410 (hereinafter $B_R$, as also shown in FIGS. 5-29, 32, and 33), where the node 408 and node 410 stem from the battery 402. In this example, each branch includes a Coulomb counter, 404, 406 where the Coulomb counter 404 for the load branch measures the amount of charge leaving the battery while the Coulomb counter 406 for the recharge branch measures the amount of charge entering the battery. The processor/controller 302 may gather this information to monitor the condition of the battery 402 as well as to report such information to the external device 102.

The node 408 sources power to several components. The processor/controller 302 receives power to operate including implementing the logic and output to control various switches that select the between the coils or coil portions and select between uplink, downlink, and recharge modes. Drive circuitry such as an oscillator, for instance a sinusoidal power amplifier, or such as a set of transmitter switches 414 receive power to ultimately ring the telemetry coil or coil portion to emit telemetry signals. A receiver 412 consumes power to receive and amplify the downlink telemetry signal and return it to the controller 302. The medical circuitry 306 receives power to perform the medical tasks such as pulse generation, drug infusion, data collection, and the like.

Several components receive control signals from the processor/controller 302. The drive circuitry 414 may receive an activation signal in the case of an oscillator. The drive circuitry may receive timed control signals, discussed in more detail below with reference to FIGS. 30 and 31 in the case of transmitter switches that alternate their states in order to ring the coil at the telemetry frequency to uplink telemetry signals. A set of receiver switches 424 receive control signals to achieve a state that allows detection of the telemetry signal of the coil at the receiver 412.

The node 410 of the recharge branch receives power from a power module 418. This power module 418 receives the recharge signal induced onto the coil or coil portion of a first tank circuit 416 by the incoming recharge signals. The power module 418 includes a rectifier, a filter, and a limiter so that the node 410 receives power that has a suitable voltage and current for recharging the battery 402.

The various switching modules of FIG. 4 have a default state such as where no control signal is present either by operation of the processor/controller 302 or as a result of a fully depleted battery 402. In the event of a depleted battery, the first tank circuit that is tuned to the recharge frequency will direct recharge energy into the rectifier of the power module 418. Thus, an attempt to recharge the IMD 108 that is currently non-operational may succeed in supplying enough recharge energy to the battery 402 to allow the processor/controller 302 to become operational and respond.

Examples of specific circuits such as those that are shown in FIGS. 5-29 and 32-33 and others that are discussed below implement the modules of FIG. 4 while providing the default state that allows for recharge at the recharge frequency. FIGS. 5-17 and 32 show circuits that utilize two tank circuits that share one or more nodes where one tank circuit is tuned to the recharge frequency and coupled to a rectifier to recharge the battery and the other tank circuit is tune to the telemetry frequency and is coupled to a receiver and/or drive circuitry to conduct telemetry sessions. FIGS. 18-29 and 33 show circuits that utilize multiple coil portions that share one or more nodes where one coil portion is used to tune to the recharge frequency and another coil portion is used to tune to the telemetry frequency. The coil of a tank circuit is coupled to a rectifier to recharge the battery and a portion of the coil portion present within the tank circuit is tuned to the telemetry frequency and is coupled to a receiver and/or drive circuitry to conduct telemetry sessions.

Figure 5:
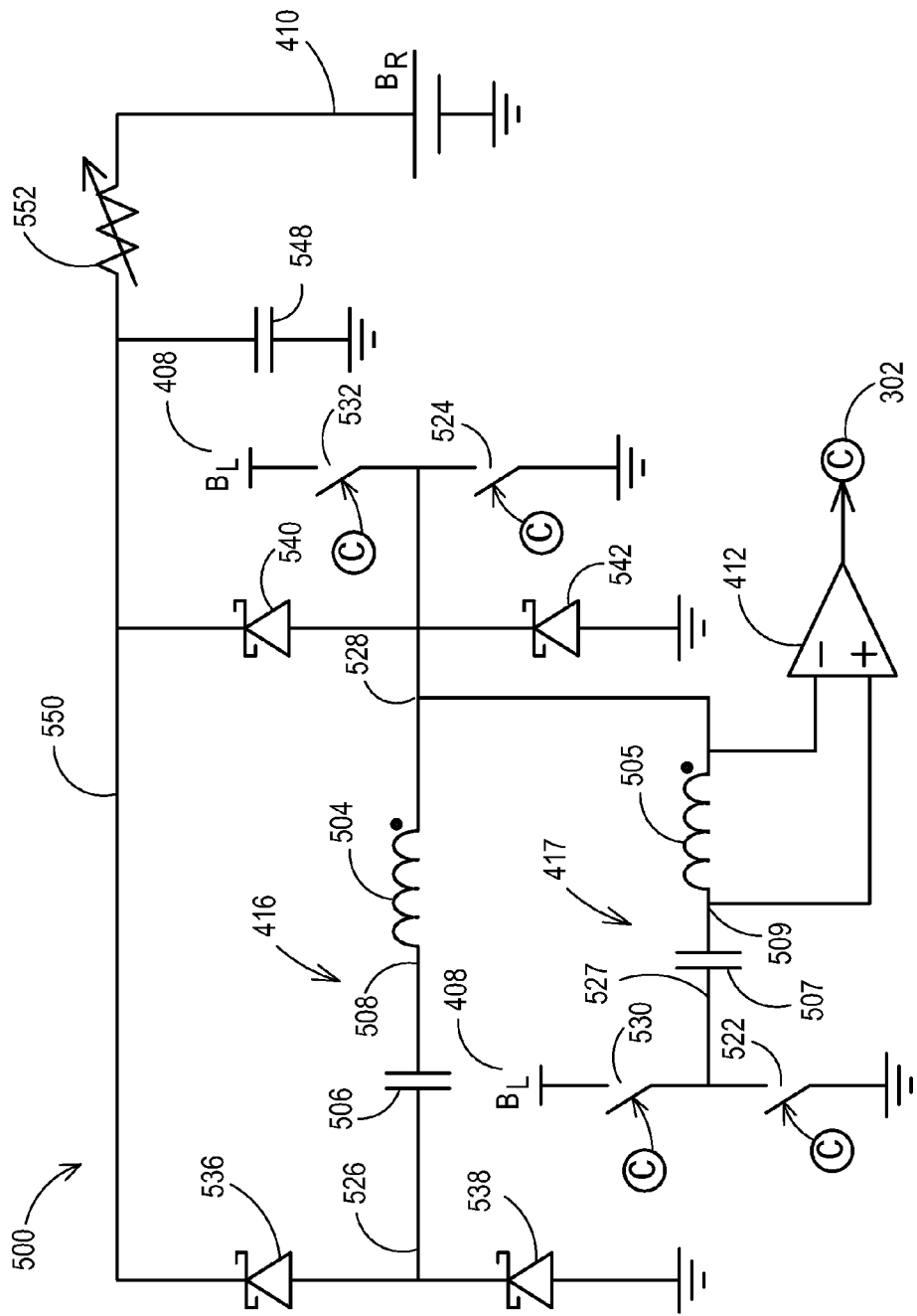
FIG. 5 shows a circuit of one example of an IMD that provides for telemetry uplink and telemetry downlink at one frequency and recharge at another frequency with multiple tank circuits and with a first receiver configuration and a first rectifier configuration.

FIG. 5 shows a first configuration 500 for a circuit that provides for telemetry uplink and downlink at a telemetry frequency as well as providing for recharge with power management at a different frequency. As discussed above, the first configuration 500 includes switches implemented in silicon with a default state that is open which allows for recharge mode to occur at the recharge frequency when the IMD 108 is non-operational due to a depleted battery.

The first configuration includes a first tank circuit 416 that has a first coil or coil portion 504 and a first capacitor 506. The first coil or coil portion 504 is either a separate coil that terminates at an inductor side node 528 or may be a portion of a larger coil where the portion 504 terminates at a tap of the larger coil where the tap forms the inductor side node 528. The first tank circuit 416 establishes several additional nodes including a first capacitor side node 526 and a first high voltage node 508. The first high voltage node 508 acquires a relatively high voltage periodically as the voltage swings within the tank circuit 416.

The first capacitor side node 526 and first inductor side node 528 are connected to a rectifier that is established by a set of diodes 536, 538, 540, and 542 that may be of the Schottky variety. These diodes form a full-bridge rectifier. However, a first inductor low side switch 524 is present and may be closed by the processor/controller 302 to provide a half-wave rectifier.

As an alternative full-wave rectifier for this configuration, a capacitor low side switch (not shown) may be added between the first capacitor side node 526 and ground. This capacitor low side switch and the inductor low side switch 524 may be operated as low-side synchronous rectifier switches. In such a case, the state machine control of these switches by the processor/controller 302 operates by closing this added capacitor low side switch while leaving the inductor low side switch 524 open when the inductor side node 528 flies high and by closing the inductor low side switch 524 while leaving the added capacitor low side switch open when the capacitor side node 526 flies high. Other rectifier options are discussed with reference to other circuit diagrams below.

The high voltage node 508 achieves the highest voltage during voltage swings within the tank circuit 416. As can be seen, no voltage sensitive device is DC coupled to the high voltage node which reduces the likelihood of any damage to those voltage sensitive devices.

The rectifier provides voltage to a rectifier recharge node 550. This rectifier recharge node 550 also includes a filtering capacitor 548 in parallel with the rectifier. A current or voltage limiter 552 is in series between the rectifier recharge node 550 and the battery recharge node 410 to prevent the battery 402 (as shown in FIG. 4 in connection with the recharge node 410) from receiving voltage and/or current in excess of the amounts rated for the battery 402.

This embodiment of the IMD 108 is also capable of telemetry downlink by using a second tank circuit 417 that includes a second coil or coil portion 505 connected to the inductor side node 528 and a second capacitor 509 connected to a second capacitor side node 527. This second coil or coil portion 505 may either be a separate coil or may be a portion of the larger coil that includes the first coil portion 504, where the first coil portion 504 is separated from the second coil portion 505 at the tap forming the inductor side node 528.

As shown, the first and second coils or coil portions 504, 505 are geometrically oriented so that the currents are in phase at the inductor side node 528 and therefore sum at that node. For a single coil forming two coil portions 504, 505 separated at the tap, this may be accomplished by changing the direction of the turns of the coil of the second coil portion 505 relative to the first coil portion 504, such as where a bobbin carrying both coil portions 504, 505 is linear. As another example, this may be accomplished by maintaining the direction of the turns about the bobbin but by reversing the direction of the bobbin at the tap such as by having a U-shape.

The distribution of windings between the first coil or coil portion 504 and the second coil or coil portion 505 is such as to optimize the corresponding recharge and telemetry operations. For example, it may be beneficial to have twice as many windings in the second coil or coil portion 505 being used for telemetry as in the first coil or coil portion 504 being used for recharge. Where there is a relatively large frequency spacing between the telemetry and recharge operations with a Q for each that is not extremely low, the resonant behavior of the two tank circuits 416, 417 does not necessarily interfere with each other so that both operations are achievable at separate times.

In some examples, the two coils or coil portions 504, 505 may be positioned closely together and with relatively small coil diameters in order to further miniaturize the size of the IMD. Therefore, having the coils 504, 504 geometrically oriented and with the currents in phase to sum at the common node 528 may increase the likelihood that the IMD adequately receives the telemetry signals or recharge energy being provided by the external device when configured so that both coils 504, 505 are producing current regardless of whether the incoming energy is at the telemetry frequency or the recharge frequency.

The receiver 412 is present to receive the telemetry signals induced on the second coil or coil portion 505. The receiver 412 is connected to the tank circuit 417 in a first configuration in the example of FIG. 5. Other configurations are discussed below with reference to other figures. In this example, a first input of the receiver 412 is connected to the inductor side node 528, which is shared with the first tank circuit 416, while a second input of the receiver 412 is connected to a second high voltage node 509 in this particular example. It will be appreciated that the relative position of the capacitor 506 and inductor 504 may be reversed within the circuit as may be the relative position of the second capacitor 507 and the second coil or coil portion 505 such that the node shared between the first tank circuit 416 and the second tank circuit 417 may be a node attached to the capacitors 506, 507 or to a capacitor of one tank circuit and a coil or coil portion of the other.

This embodiment of the IMD 108 is also capable of telemetry uplink by using the tank circuit 417 and one of various methods. For instance, as shown, an H-bridge may be provided in relation to the tank circuit 417 by connecting a capacitor high side switch 530 between the load node 408 and the capacitor side node 527 while also connecting an inductor high side switch 532 between the load node 408 and the inductor side node 528.

The various modes of operation of the configuration 500 operate as follows. During recharge mode when using full wave rectification, the processor/controller 302 of this example allows all switches to remain open. As a result, the current of the tank circuit 416 passes through the rectifier and on to the limiter 552 and ultimately to the battery 402 (as shown in FIG. 4 in connection with the recharge node 410). If half wave rectification is desired, then the inductor low side switch 524 is closed.

During telemetry downlink, the processor/controller 302 of this example leaves the capacitor high side switch 530 and inductor high side switch 532 in their open states while closing the capacitor low side switch 522 and the inductor low side switch 524. This effectively grounds the second tank circuit 417 which allows current to flow in response to receiving telemetry signals on the telemetry coil or coil portion 505. During telemetry downlink, the capacitor side node 526 is allowed to float within a diode drop below ground and above rectifier recharge node 550, respectively. Meanwhile, the receiver 412 picks up the differential voltage across the telemetry coil or coil portion 505. Several other methods of telemetry downlink are discussed below with reference to other circuit diagrams.

During telemetry uplink, the H-bridge may be operated by opening the capacitor high side switch 530 and the inductor low side switch 524 while the inductor high side switch 532 and the capacitor low side switch 522 are closed. After a set amount of time defined by the telemetry frequency, the inductor high side switch 532 and the capacitor low side switch 522 are opened while the capacitor high side switch 530 and the inductor low side switch 524 are closed. These pairings continue to alternate states to ring up the telemetry coil or coil portion 505 and allow it to emit for a set amount of time. The capacitor low side switch 522 and the inductor low side switch 524 are then closed to ring down the telemetry coil or coil portion 505, which remains off for a set period until time to again ring up the telemetry coil or coil portion 505. In this manner, a carrier on/off protocol can be effectively implemented to uplink data. As an alternative, the telemetry coil or coil portion 505 may be allowed to ring down by closing a tank switch 520 discussed in more detail below with reference to FIG. 33 and FIG. 8 or by opening all switches and allowing the second tank circuit 417 to ring down at its natural frequency.

Figure 30:
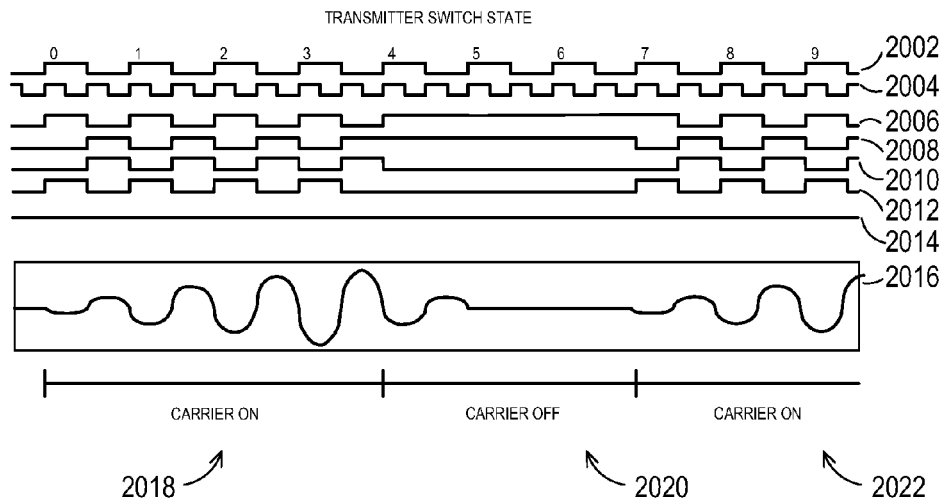
FIG. 30 shows a state of switches of one example of an IMD to establish telemetry uplink.

FIG. 30 shows a first timing chart for the H-bridge manner of telemetry uplink. The first waveform 2002 is a clock signal that is set to the telemetry frequency. The second waveform 2004 is a clock signal that is set to double the telemetry frequency but is unused in this particular method. The third and fourth waveforms 2006, 2008 correspond to the state of the capacitor low side switch 522 and the inductor low side switch 524, where a high value represents a closed state and a low value represents an open state. The fifth and sixth waveforms 2010, 2012 correspond to the state of the capacitor high side switch 530 and the inductor high side switch 532. The seventh waveform 2014 corresponds to the state of a tank switch 520, discussed below in relation to other embodiments which remains open in this example.

The eighth waveform 2016 corresponds to the current through the telemetry coil 505. Sections 2018 and 2022 correspond to the ringing up and carrier on periods, while section 2020 corresponds to the carrier off period.

Figure 31:
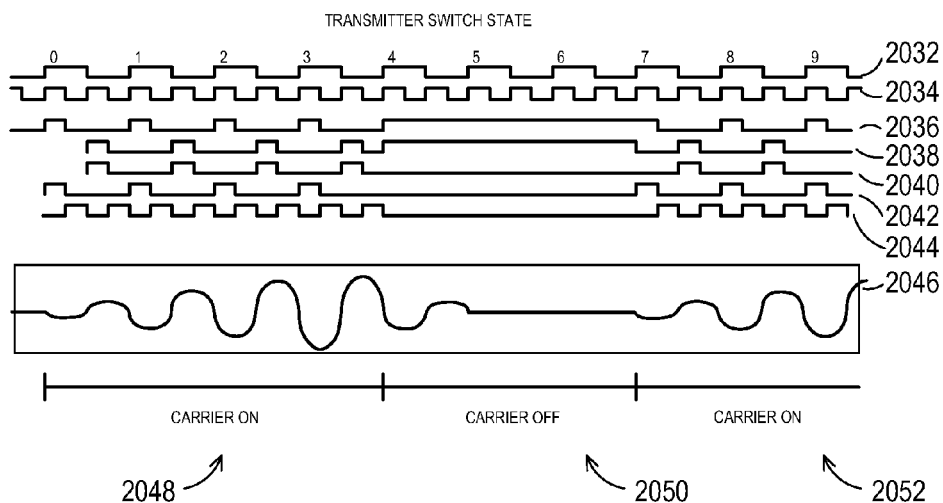
FIG. 31 shows an alternative state of switches of one example of an IMD to establish telemetry uplink.

FIG. 31 shows an alternative timing chart for the H-bridge manner of telemetry uplink where the transmission power is being throttled down by reducing the drive time of the telemetry coil 505. In this particular example, the drive time is being reduced by 50% by application of a clock frequency double that of the telemetry frequency, but other drive time reductions are applicable. Throttling down the transmission power may be done for various reasons, such as to reduce the range of the transmission for security or other purposes and/or to conserve energy. The drive time may be reduced more or less than the 50% shown in FIG. 31 for similar reasons.

The first waveform 2032 is a clock signal that is set to the telemetry frequency. The second waveform 2034 is a clock signal that is set to double the telemetry frequency. The third and fourth waveforms 2036, 2038 correspond to the state of the capacitor low side switch 522 and the inductor low side switch 524, where a high value represents a closed state and a low value represents an open state. The fifth and sixth waveforms 2040, 2042 correspond to the state of the capacitor high side switch 530 and the inductor high side switch 532. The seventh waveform 2044 corresponds to the state of the tank switch 520.

The eighth waveform 2046 corresponds to the current through the telemetry coil 505. Sections 2048 and 2052 correspond to the ringing up and carrier on periods, while section 2050 corresponds to the carrier off period.

As can be seen, the H-bridge switches are closed for half as long as in the example of FIG. 30, and the tank switch 520 that is discussed below is closed for the remaining half of each telemetry clock cycle portion when all the H-bridge switches are open. As a result, the current in the coil 505 rings up to a fraction of the amount of current achieved in the example of FIG. 30.

The telemetry uplink may be established in other ways as well by using switches on either side of the second tank circuit 417 to ring the coil 505. For example, the capacitor low side switch 522 and the inductor high side switch 532 may be briefly closed, then opened while leaving the other switches open and then letting the second tank circuit 417 ring down by closing both the capacitor low side switch 522 and the inductor low side switch 524.

Figure 6:
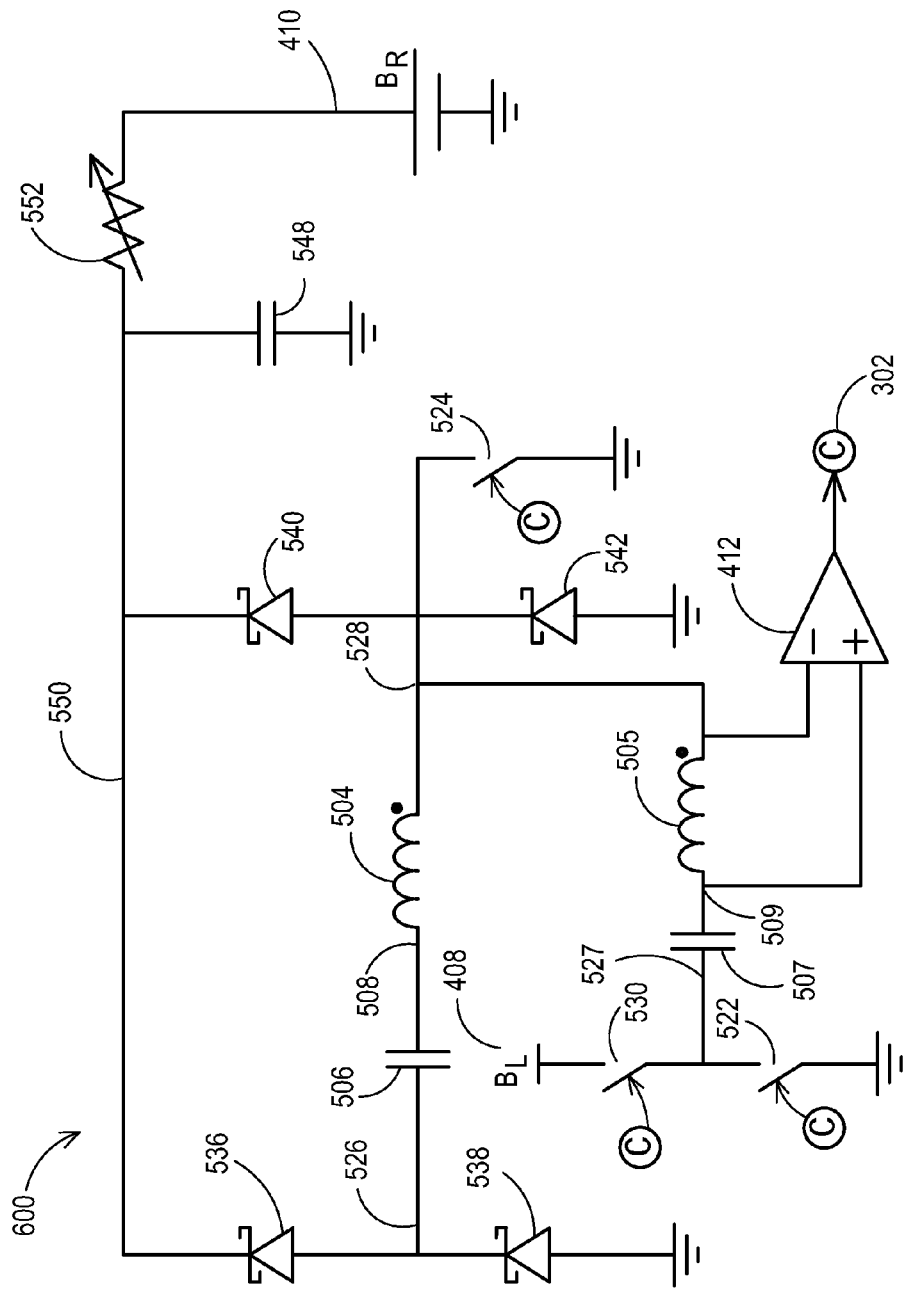
FIG. 6 shows a circuit of one example of an IMD that provides for telemetry uplink and telemetry downlink at one frequency and recharge at another frequency with multiple tank circuits and with a first receiver configuration, a first rectifier configuration, and an alternative uplink switch configuration.

FIG. 6 shows another configuration 600 that is the same as the configuration 500 of FIG. 5 except that the H-bridge drive circuit of FIG. 5 is now a half-wave drive by removal of the inductor high side switch 532 and by alternately closing the capacitor high side switch 530 and the capacitor low side switch 522 while keeping the inductor low side switch 524 closed. This may be beneficial where it is inconvenient to have a high side switch on the inductor side node 528.

Figure 7:
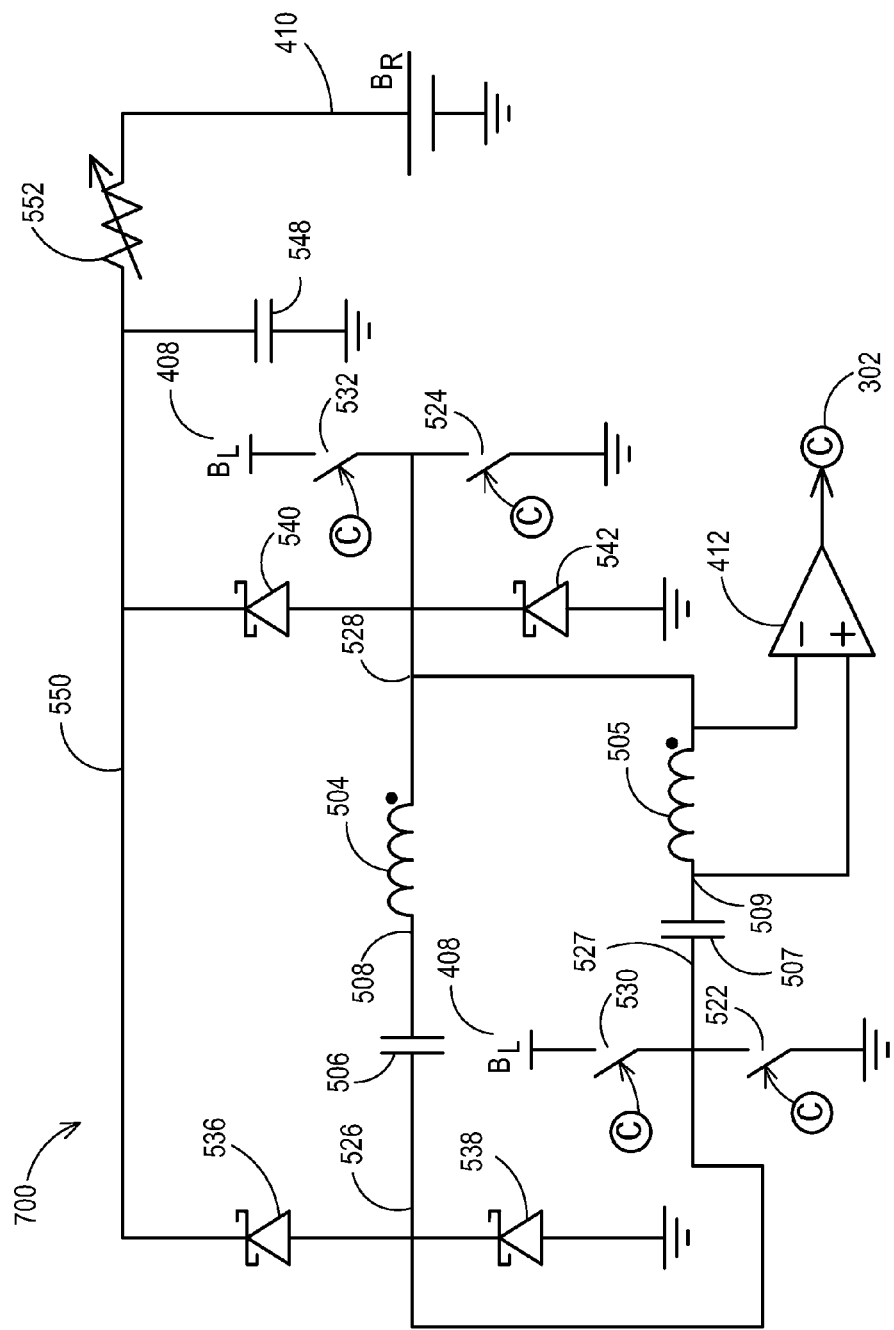
FIG. 7 shows a circuit of one example of an IMD that provides for telemetry uplink and telemetry downlink at one frequency and recharge at another frequency with multiple tank circuits and with a first receiver configuration, a first rectifier configuration, and an alternative tank circuit configuration.

FIG. 7 shows another configuration 700 that is the same as the configuration 500 of FIG. 5 except that the first capacitor side node 526 and the second capacitor side node 527 are coupled together as one node. As a result, the voltage at this one node is constrained during telemetry to a diode drop below ground and a diode drop above the recharge node 550. As stated above, the first coil or coil portion 504 and the second coil or coil portion 505 are geometrically oriented to avoid cancellation of energy through interaction of the two tank circuits 416, 417.

Figure 8:
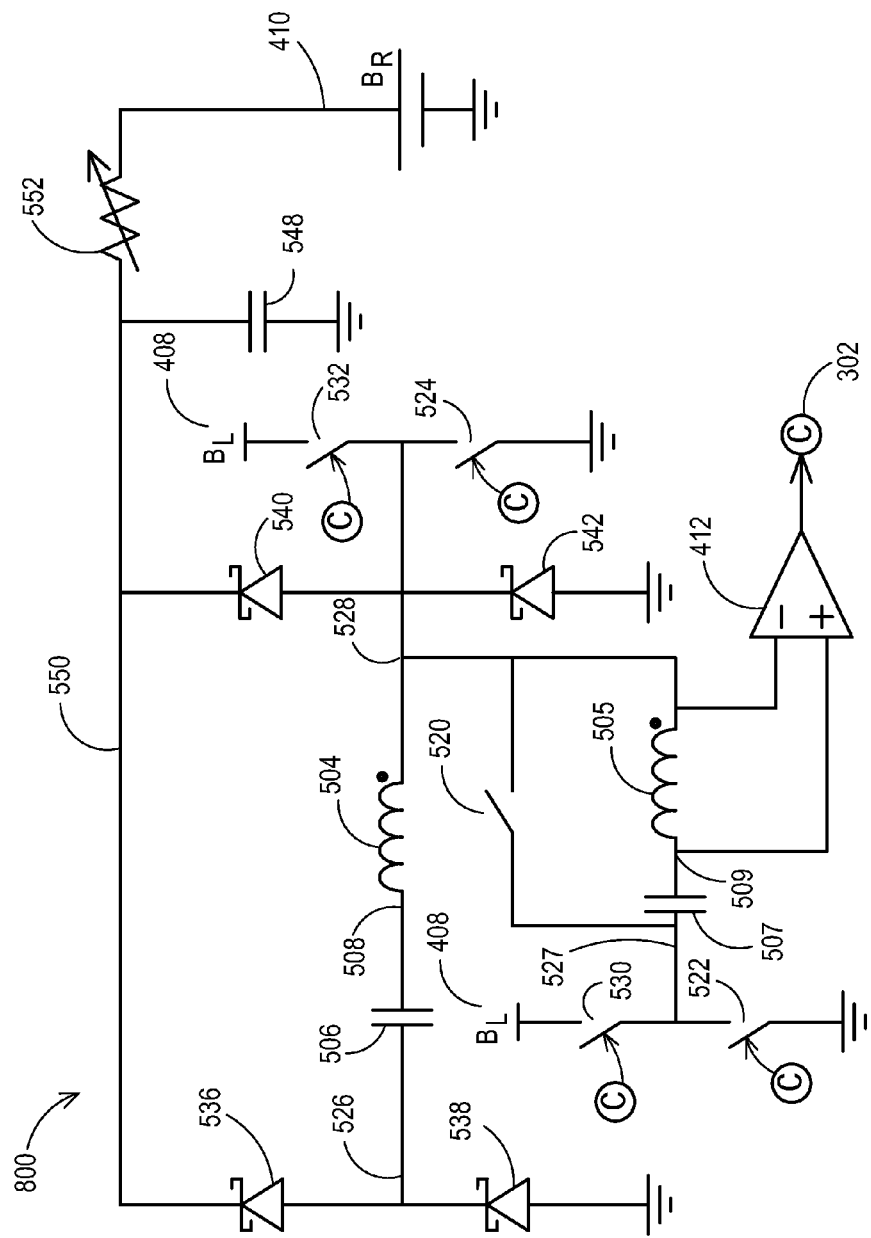
FIG. 8 shows a circuit of one example of an IMD that provides for telemetry uplink and telemetry downlink at one frequency and recharge at another frequency with multiple tank circuits and with a first receiver configuration, a first rectifier configuration, and an alternative downlink switch configuration.

FIG. 8 shows another configuration 800 that is the same as the configuration 500 of FIG. 5 except that the tank switch 520 mentioned above is included. The tank switch 520 extends from the capacitor side node 527 to the inductor side node 528 and may be closed to ring down the second tank circuit 417 during uplink or to allow current to flow through the tank circuit 417 during downlink, as opposed to closing the capacitor low side switch 522 and the inductor low side switch 524. The operation and timing of the tank switch 520 during uplink is discussed above in relation to FIG. 31. The tank switch 520 may remain open during recharge.

Figure 9:
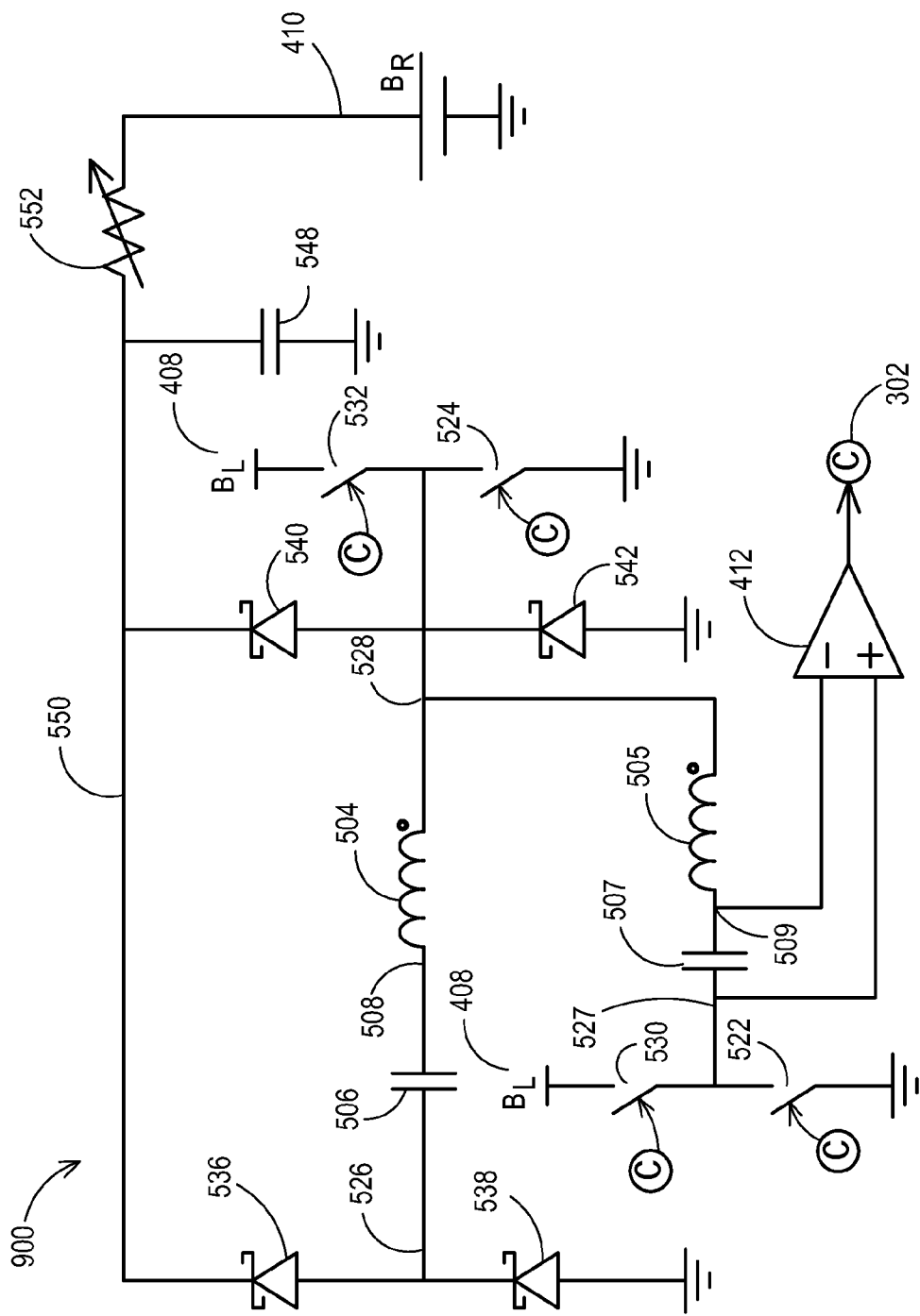
FIG. 9 shows a circuit of one example of an IMD that provides for telemetry uplink and telemetry downlink at one frequency and recharge at another frequency with multiple tank circuits and with a second receiver configuration and a first rectifier configuration.

FIG. 9 shows another configuration 900 that is the same as the configuration 500 of FIG. 5 except that the receiver's connectivity is configured differently. In this example, a receiver input is coupled directly to the second high voltage node 509, and both the capacitor side node 527 and the inductor side node 528 are connected to ground by closing switches 522 and 524 or by closing the tank switch 520 if present when receiving telemetry signals while all other switches are open. However, the other input of the receiver 412 is connected to the capacitor side node 527 rather than the inductor side node 528.

Figure 10:
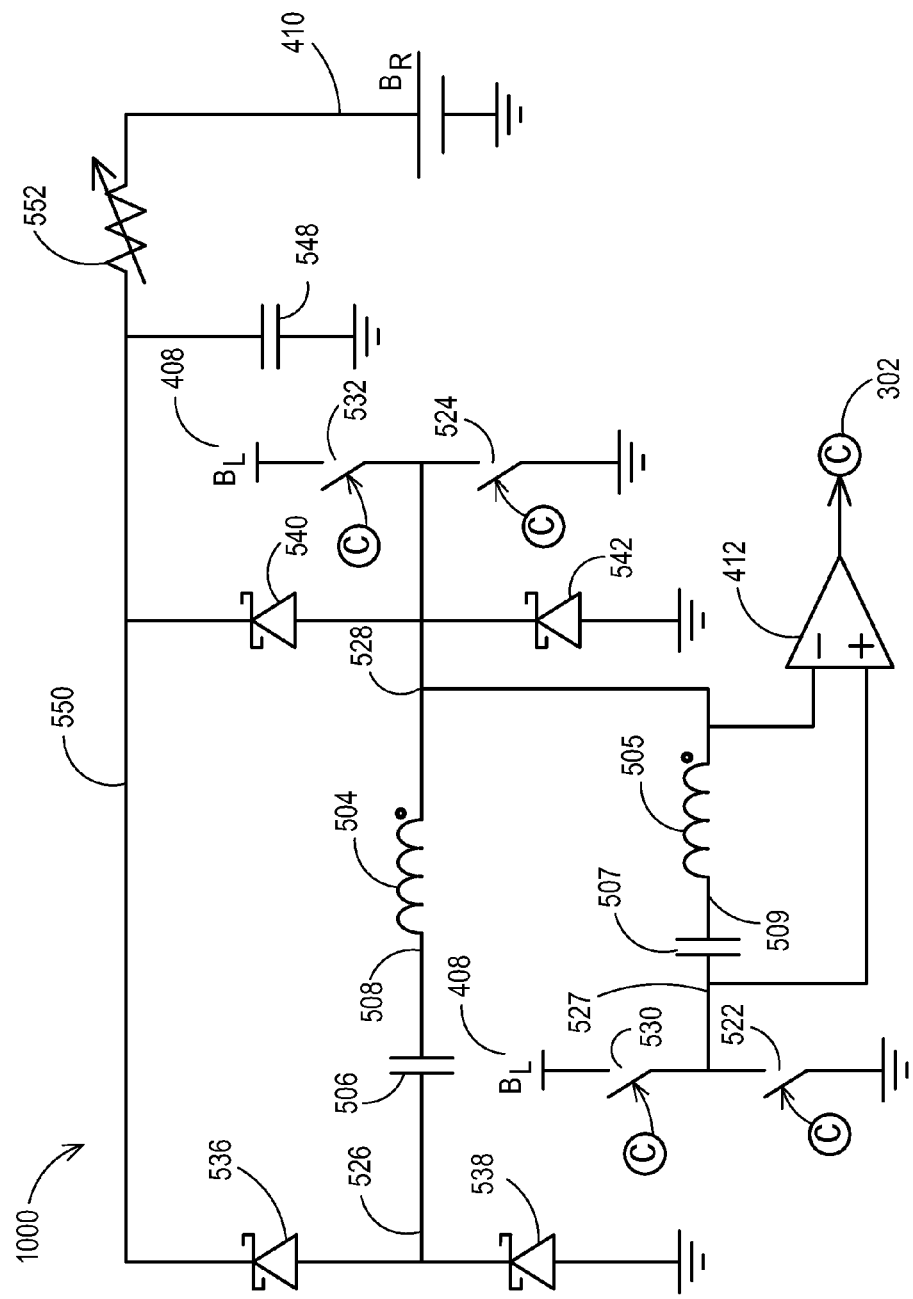
FIG. 10 shows a circuit of one example of an IMD that provides for telemetry uplink and telemetry downlink at one frequency and recharge at another frequency with multiple tank circuits and with a third receiver configuration and a first rectifier configuration.

FIG. 10 shows another configuration 1000 that is the same as the configuration 500 of FIG. 5 except that the receiver's connectivity is configured differently. Here, the receiver 412 is connected differentially across the tank circuit 417 by having a receiver input coupled directly to the inductor side node 528 while another receiver input is coupled directly to the capacitor side node 527. All other switches are open when receiving telemetry signals or tank switch 520 may be closed if present.

Figure 11:
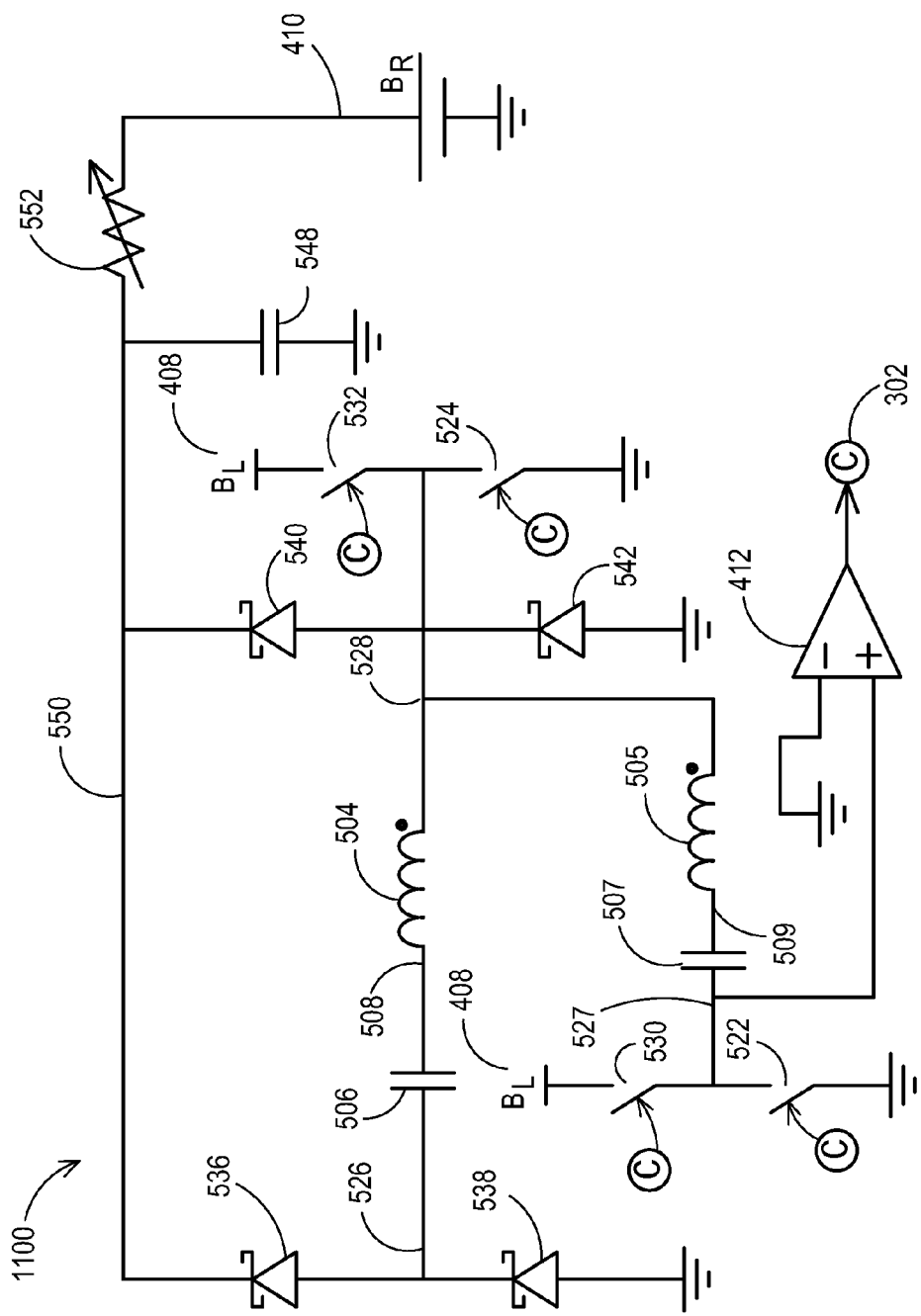
FIG. 11 shows a circuit of one example of an IMD that provides for telemetry uplink and telemetry downlink at one frequency and recharge at another frequency with multiple tank circuits and with a fourth receiver configuration and a first rectifier configuration.

FIG. 11 shows another configuration 1100 that is the same as the configuration 500 of FIG. 5 except that the receiver's connectivity is configured differently. Here, one input of the receiver 412 is connected to the capacitor side node 527 while the other input of the receiver 412 is connected to ground. All other switches are open when receiving telemetry signals or tank switch 520 may be closed if present.

Figure 12:
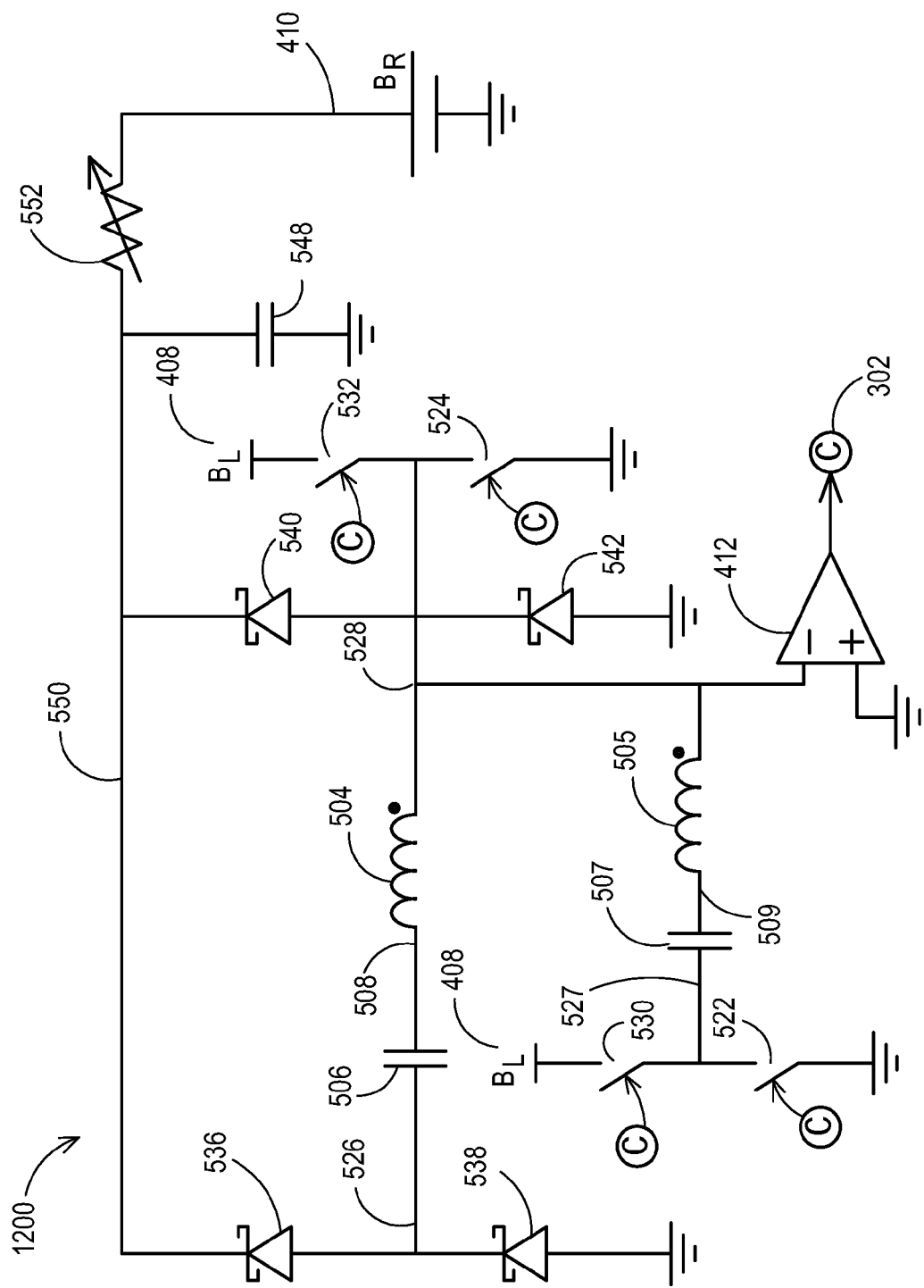
FIG. 12 shows a circuit of one example of an IMD that provides for telemetry uplink and telemetry downlink at one frequency and recharge at another frequency with multiple tank circuits and with a fifth receiver configuration and a first rectifier configuration.

FIG. 12 shows another configuration 1200 that is the same as the configuration 500 of FIG. 5 except that the receiver's connectivity is configured differently. Here, one input of the receiver 412 is connected to the inductor side node 528 while the other input of the receiver 412 is connected to ground. All other switches are open when receiving telemetry signals or tank switch 520 may be closed if present.

Figure 13:
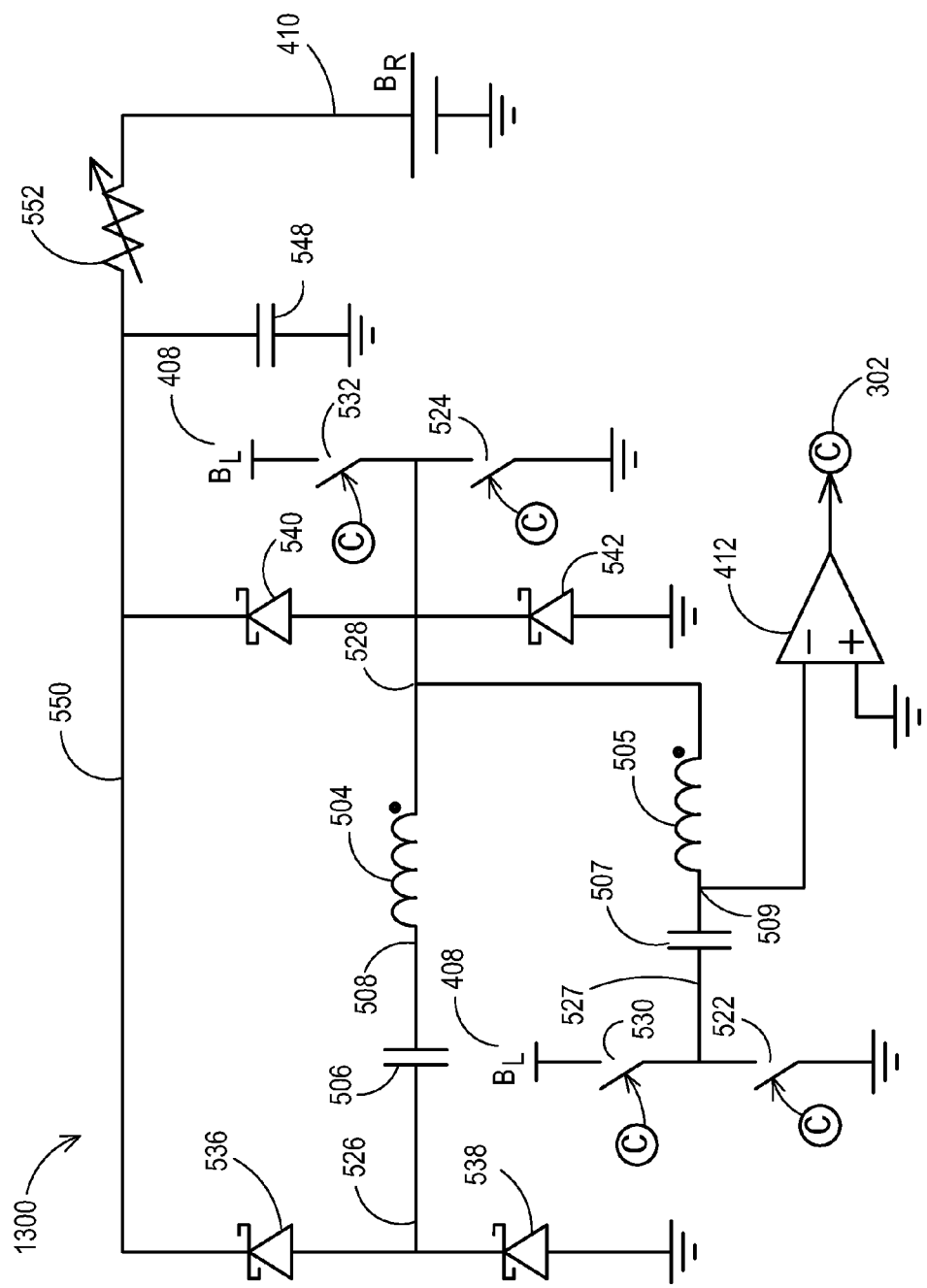
FIG. 13 shows a circuit of one example of an IMD that provides for telemetry uplink and telemetry downlink at one frequency and recharge at another frequency with multiple tank circuits and with a sixth receiver configuration and a first rectifier configuration.

FIG. 13 shows another configuration 1300 that is the same as the configuration 500 of FIG. 5 except that the receiver's connectivity is configured differently. Here, one input of the receiver 412 is connected directly to the second high voltage node 509 while the other input of the receiver 412 is connected to ground. All other switches are open when receiving telemetry signals or tank switch 520 may be closed if present.

Figure 14:
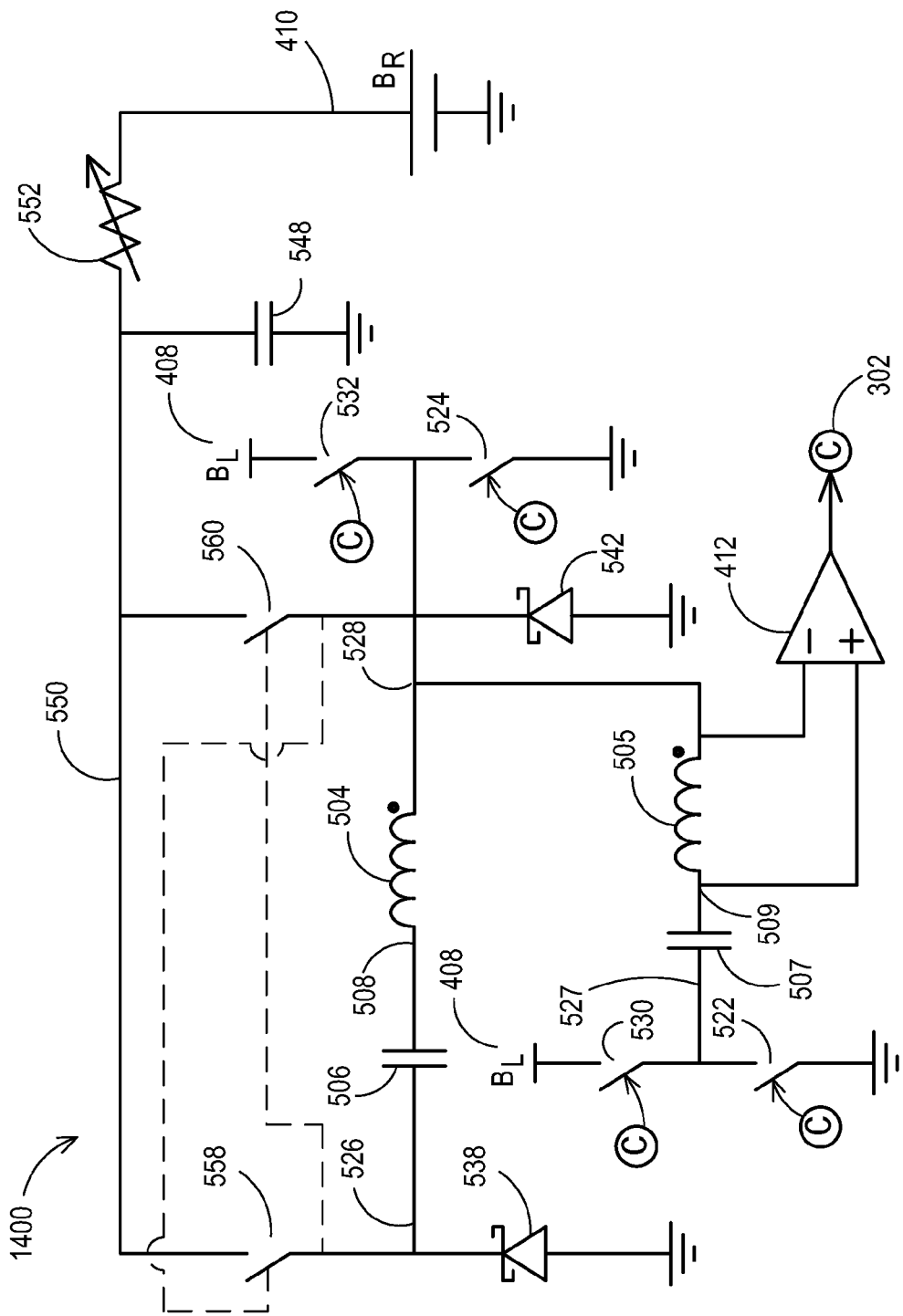
FIG. 14 shows a circuit of one example of an IMD that provides for telemetry uplink and telemetry downlink at one frequency and recharge at another frequency with multiple tank circuits and with a first receiver configuration and a second rectifier configuration.

FIG. 14 shows a configuration 1400 that is the same as the configuration 500 of FIG. 5 except that the rectifier is different. In this configuration 1400, the rectifier may use high side synchronous rectification by including a capacitor high side rectifier switch 558 and an inductor high side rectifier switch 560 in place of high side diodes. As discussed for the configuration of FIG. 5, a capacitor low side switch (not shown) may be added between the capacitor side node 526 and ground so that this added capacitor low side switch and the inductor low side switch 524 may operate to provide the low side synchronous rectification.

In this particular example, the low side synchronous rectifier switches may be N-MOS devices while the high side synchronous rectifier switches 558, 560 may be P-MOS devices. The result based on the state machine control by the processor/controller 302 is that when the inductor side flies high, the inductor high side switch 560 and the added capacitor low side switch are closed while the capacitor high side switch 558 and the inductor low side switch 524 are open. When the capacitor side flies high, the capacitor high side switch 558 and the inductor low side switch 524 are closed while the inductor high side switch 560 and the added capacitor low side switch are open.

The synchronous rectifier of FIG. 14 may be a pure full wave synchronous rectifier as another alternative. In that case, the diodes 538 and 542 are omitted.

While this operation of these switches 524, 558, and 560 applies to recharge, during uplink and downlink telemetry operations, the added capacitor low side switch and the inductor low side switch 524 may operate in the same manner as discussed above in relation to FIG. 5. The capacitor high side switch 558 and the inductor high side switch 560 may remain open during uplink and downlink telemetry operations.

Figure 15:
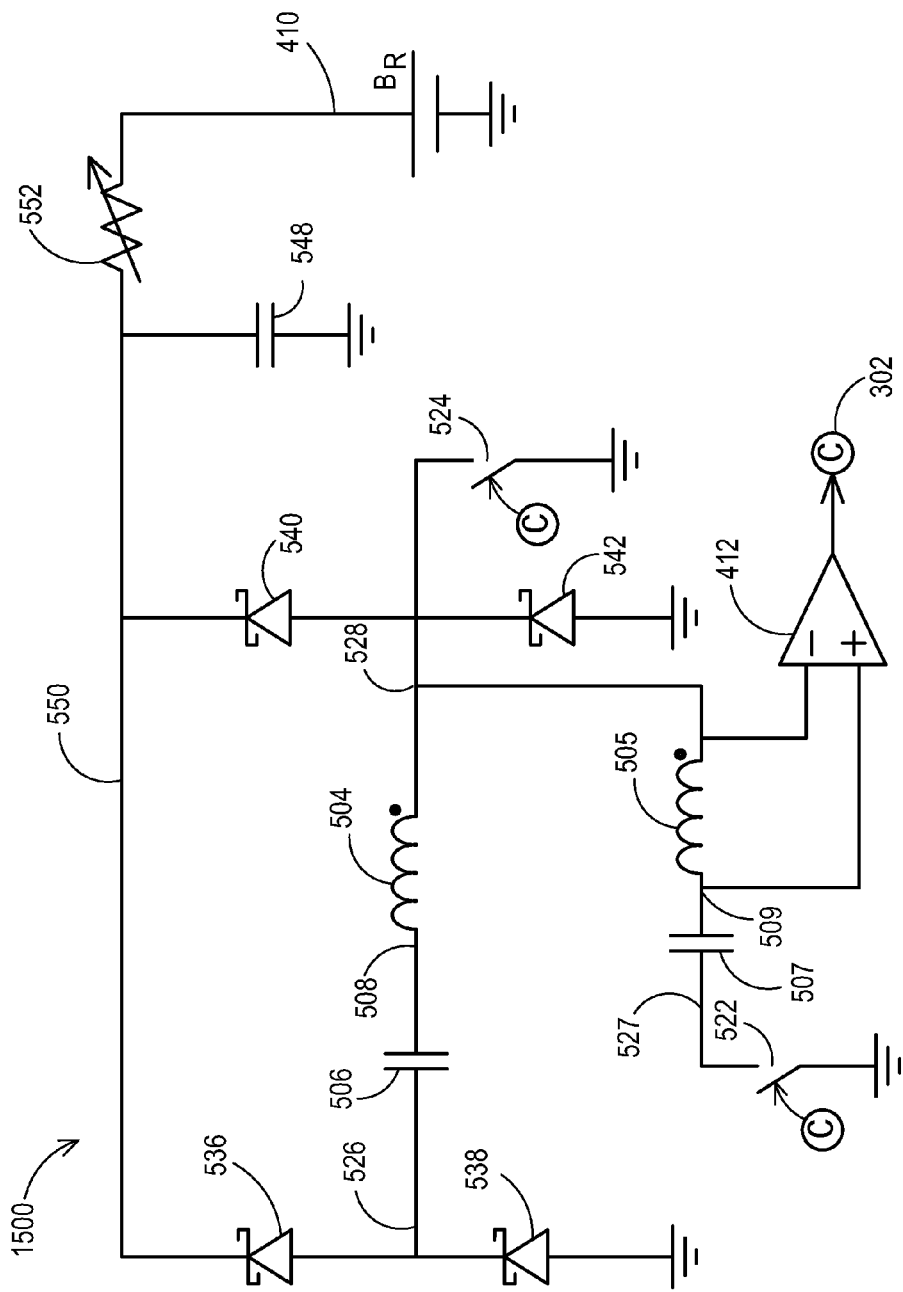
FIG. 15 shows a circuit of one example of an IMD that provides for telemetry downlink at one frequency and recharge at another frequency with multiple tank circuits and with a first receiver configuration and a first rectifier configuration.

FIG. 15 shows another configuration 1500 like the configuration 500 of FIG. 5, except that the high side of the H-bridge created by the capacitor high side switch 530 and inductor high side switch 532 has been omitted. In this situation, the second coil or coil portion 505 is being used for downlink telemetry. Uplink telemetry may be unnecessary in some contexts for an IMD 108. As another example, uplink telemetry may be provided at a separate frequency than downlink telemetry and may utilize a separate circuit and coil from that shown so that full-duplex communication with the external device 102 may be achieved. The variations discussed above in FIGS. 5-14 and below in FIG. 17 are also applicable to the configuration 1500 to the extent those variations relate to recharging and telemetry downlink.

Figure 16:
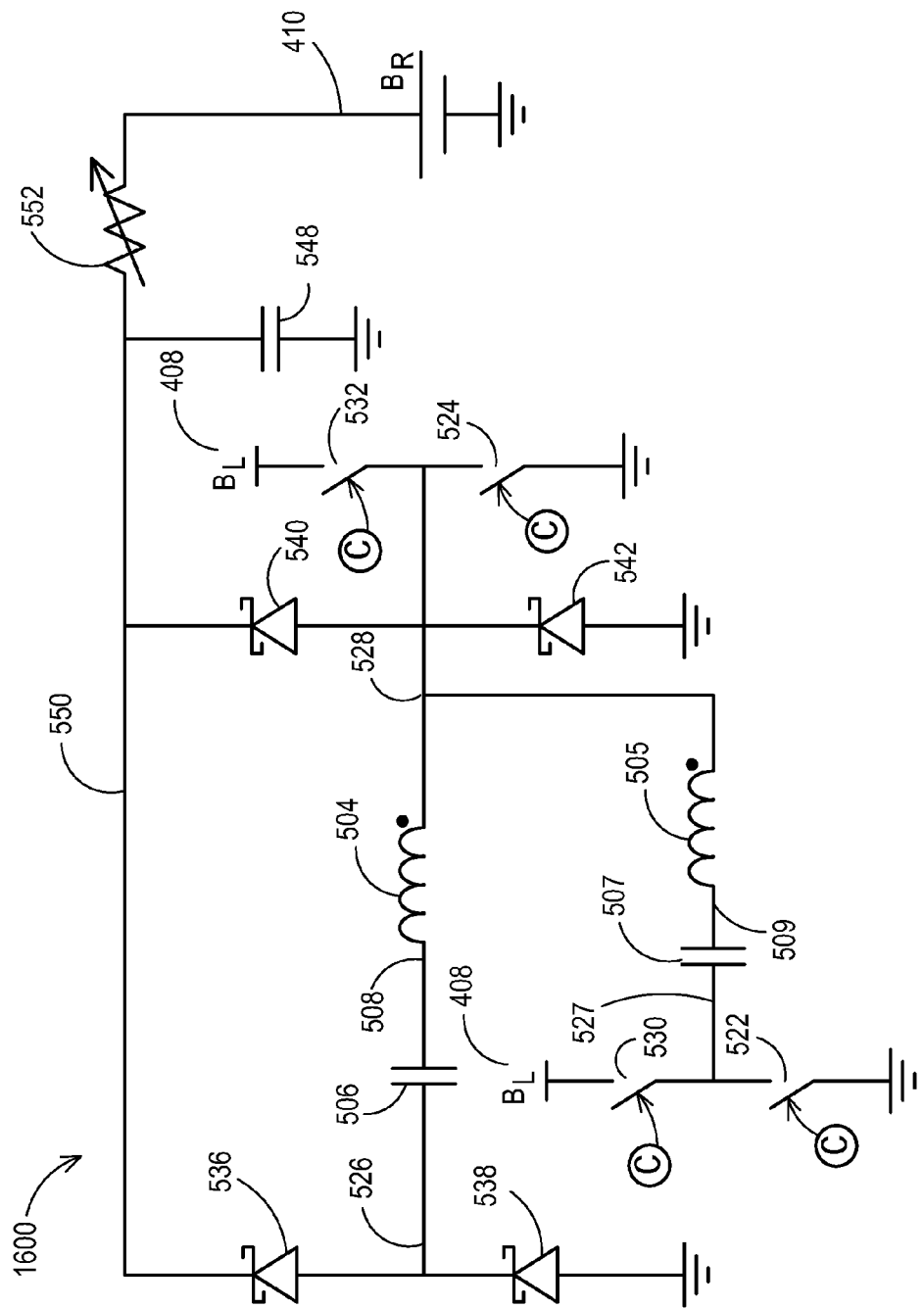
FIG. 16 shows a circuit of one example of an IMD that provides for telemetry uplink at one frequency and recharge at another frequency with multiple tank circuits and a first rectifier configuration.

FIG. 16 shows another configuration 1600 like the configuration 500 of FIG. 5, except that the receiver 412 has been omitted. In this situation, the second coil or coil portion 505 is being used for uplink telemetry. Downlink telemetry may be unnecessary in some contexts for an IMD 108. As another example, downlink telemetry may be provided at a separate frequency than uplink telemetry and may utilize a separate circuit and coil from that shown so that full-duplex communication with the external device 102 may be achieved. The variations discussed above in FIGS. 5-14 and 17 are also applicable to the configuration 1600 to the extent those variations relate to recharging and telemetry uplink.

Figure 17:
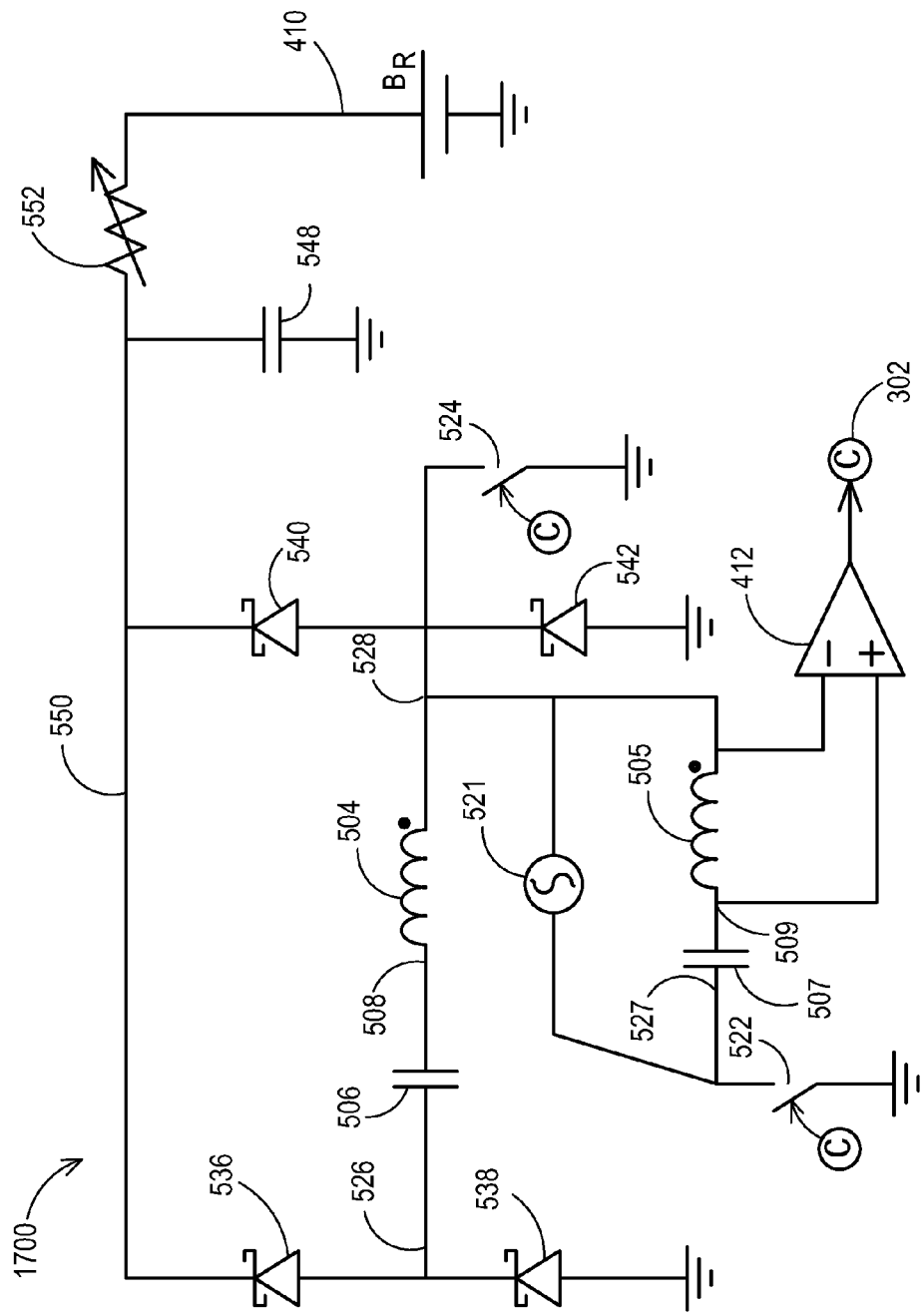
FIG. 17 shows a circuit of one example of an IMD that provides for telemetry uplink and telemetry downlink at one frequency and recharge at another frequency with multiple tank circuits and with a first receiver configuration, a first rectifier configuration, and with an oscillator for uplink.

FIG. 17 shows another configuration 1700 like the configuration 500 of FIG. 5 except that the transmission switches 522, 524, 530, and 532 are no longer being used to ring the second coil or coil portion 505. Instead, an oscillator 521 such as a sinusoidal power amplifier is connected across the second tank circuit 417 to drive the second tank circuit 417 at the uplink frequency. The oscillator 521 may be activated and deactivated by the controller 302 which may also switch the oscillator 521 into and out of the circuit. The capacitor high side switch 530 and the inductor high side switch 532 may be omitted as shown. This oscillator 521 may result in fewer harmonics on the uplink carrier. It will be appreciated that all of the variations discussed above in FIGS. 5-16 are also applicable to the example of FIG. 17.

Figure 32:
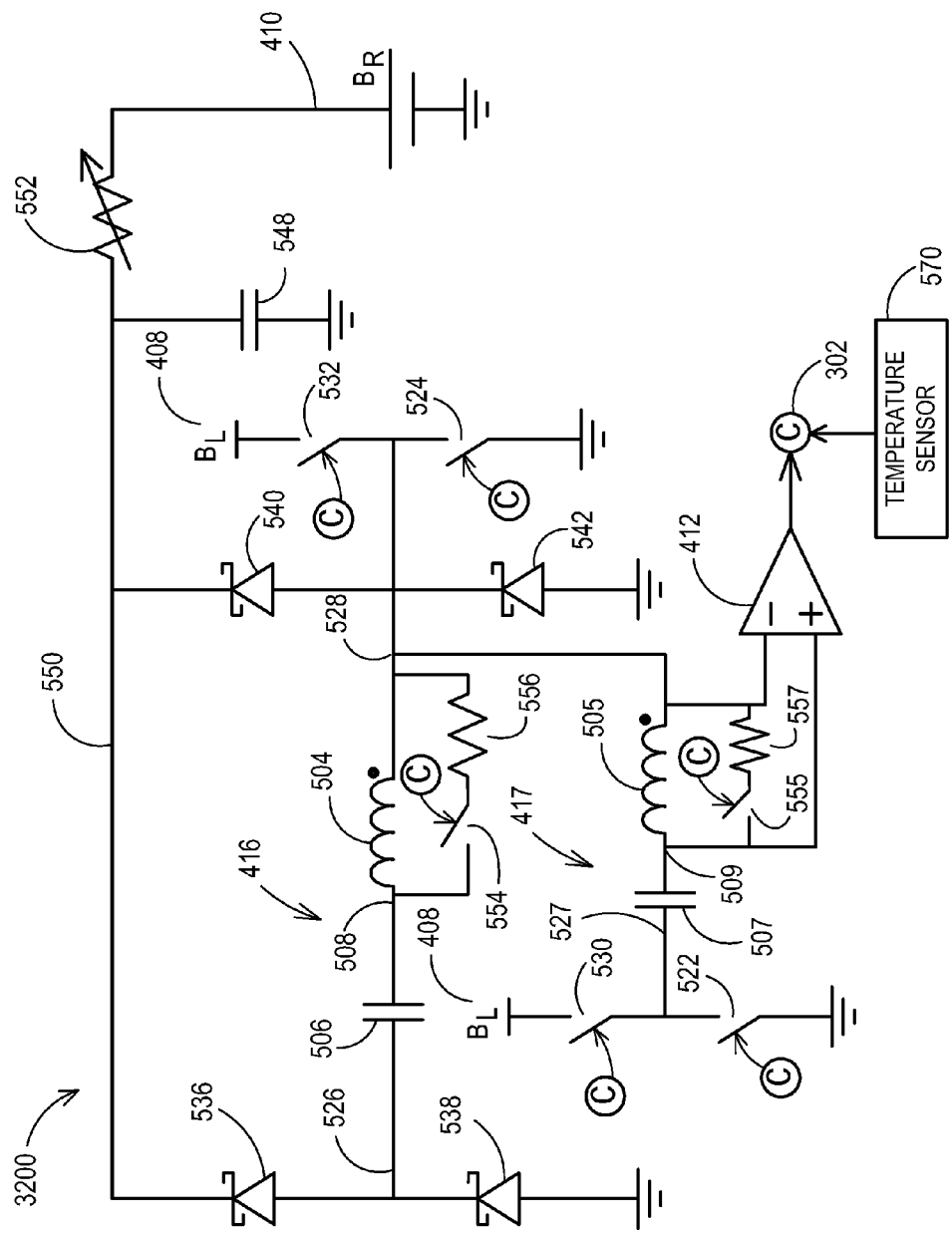
FIG. 32 shows a circuit of one example of an IMD that that provides for telemetry uplink and telemetry downlink at one frequency and recharge at another frequency with multiple tank circuits, a first receiver configuration, a first rectifier configuration and including a first snubbing resistor for power management and a second snubbing resistor for telemetry uplink.

FIG. 32 shows a second configuration 3200 which is identical to the first configuration 500 of FIG. 5 except that a circuit pathway is provided that includes a snubbing resistor 556 and a snubbing switch 554 that is under control of the processor/controller 302 in parallel with the coil 504. This circuit pathway provides power management in the event of an overcharge condition. Because the snubbing switch 554 may be closed to allow some tank circuit current to pass through the snubbing resistor to dissipate the energy as heat in that component and to lower the Q of the tank circuit 416, there is less energy to be dissipated elsewhere.

Another circuit pathway including a second snubbing switch 555 and second snubbing resistor 557 may also be provided. The telemetry of the external device 102 may be configured to receive information by monitoring for a change in the mutual inductance between the coil of the external device 102 and the coil or coil portion 505 of the IMD 108 that is caused by the IMD 108 while the external device 102 is emitting a signal. This change in the mutual inductance by the IMD 108 can be viewed as a transmission of information, for example where an on-off fashion of the change in mutual inductance is similar to a carrier on-off protocol. In such a case, the H-bridge may be unnecessary and the capacitor high side switch 530 and inductor high side switch 532 may be omitted, although low side switches 522 and 524 may be retained for other purposes such as to ground the tank circuit 417.

The circuit pathway including the second snubbing switch 555 and the second snubbing resistor 557 is shown in the configuration 3200 of FIG. 32 as a modification to the configuration 500 of FIG. 5. However, it will be appreciated that this circuit pathway may be included as a modification to other configurations as well, including those discussed above in relation to FIGS. 6-17.

Figure 18:
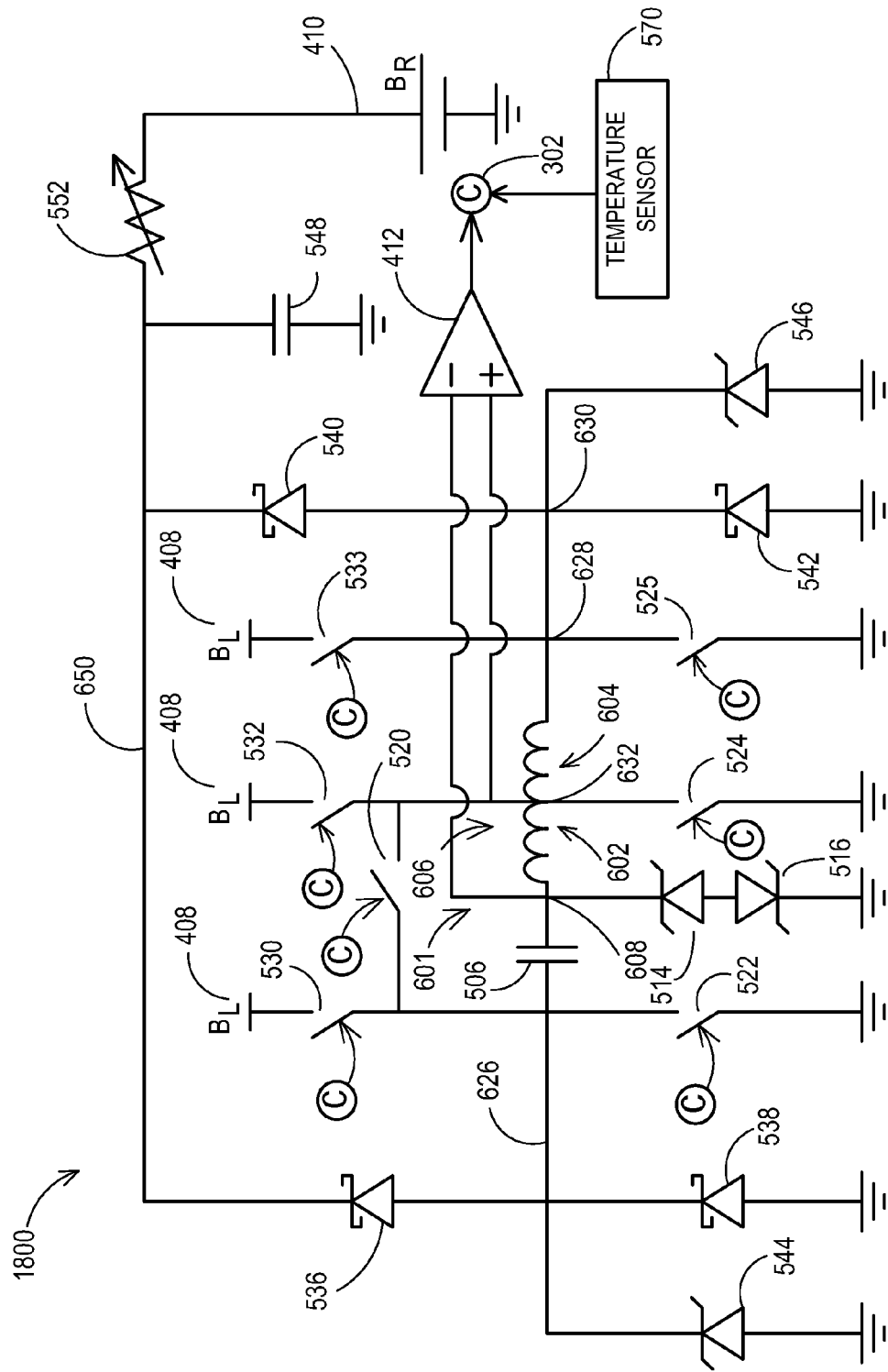
FIG. 18 shows a circuit of one example of an IMD that provides for telemetry uplink and telemetry downlink at one frequency and recharge at another frequency with multiple coil portions, with a first receiver configuration, and a first rectifier configuration.

FIG. 18 shows a first configuration 1800 for another circuit that provides for telemetry uplink and downlink at a telemetry frequency as well as providing for recharge with power management at a different frequency while using coils or coil portions. This first configuration 1800 also includes switches implemented in silicon with a default state that is open which allows for recharge mode to occur at the telemetry frequency when the IMD 108 is non-operational due to a depleted battery.

The first configuration 1800 includes a tank circuit 601 that has a coil 606 with a tap providing a tap node 632 and defining a first coil portion 602 and a second coil portion 604. It will be appreciated that rather than using a single coil with a tap, two separate coils may be used in series with the tap node 632 existing between the two coils.

In this particular example, the telemetry frequency is higher than the recharge frequency and so that only the first coil portion 602 is used during telemetry while both coil portions 602, 604 are used during recharge. It will be appreciated that the reverse may also be true and in that case the positions of some components are interchanged.

The tank circuit 601 establishes several nodes. An inductor side node 628 (which is the same node as node 630 in FIGS. 18-29 and 33), a capacitor side node 626, and a high voltage node 608 are achieved. The high voltage node 608 acquires a relatively high voltage periodically as the voltage swings within the tank circuit 601.

The capacitor side node 626 and inductor side node 628 are connected to a rectifier that is established by a set of diodes 536, 538, 540, and 542 that may be of the Schottky variety. These diodes form a full-bridge rectifier. However, a capacitor low side switch 522 and a first inductor low side switch 525 are present and either one may be closed by the processor/controller 302 to provide a half-wave rectifier.

As an alternative rectifier for this configuration, the capacitor low side switch 522 and the inductor low side switch 525 may be operated as low-side synchronous rectifier switches. In such a case, the state machine control of these switches 522, 525 by the processor/controller 302 operates by closing the capacitor low side switch 522 while leaving the inductor low side switch 525 open when the inductor side node 628 flies high and by closing the inductor low side switch 524 while leaving the capacitor low side switch 522 open when the capacitor side node 626 flies high. Other rectifier options are discussed with reference to other circuit diagrams below.

A capacitor side Zener diode 544 and an inductor side Zener diode 546 are also present. These devices limit voltage swings on the capacitor side node 626 and the inductor side node 628 to prevent over-voltage damage from occurring on voltage sensitive devices connected to these nodes. Voltage sensitive devices may include the various switches which are implemented in silicon and particularly those that are implemented as monolithic devices. Likewise, Zener diodes 514 and 516, shown in an anode-to-anode relationship but could be in a cathode-to-cathode relationship, are present to prevent over-voltage damage from occurring on additional voltage sensitive devices such as a telemetry switch 524 on the tap node 632. These devices may be actual Zener diodes or may be other devices which have Zener-like behavior.

The high voltage node 608 achieves the highest voltage during voltage swings within the tank circuit 601. As can be seen, no voltage sensitive device is directly coupled to the high voltage node which reduces the likelihood of any damage to those voltage sensitive devices.

The rectifier provides voltage to a rectifier recharge node 650. This rectifier recharge node 650 also includes the filtering capacitor 548 in parallel with the rectifier. The current or voltage limiter 552 is in series between the rectifier recharge node 650 and the battery recharge node 410 to prevent the battery 402 (as shown in FIG. 4 in connection with the recharge node 410) from receiving voltage and/or current in excess of the amounts rated for the battery 402.

This embodiment of the IMD 108 is also capable of telemetry downlink by using the tank circuit 601, albeit with less inductance in this particular example. The receiver 412 is present to receive the telemetry signals induced on the coil 606 and specifically on the first portion 602. The receiver 412 is connected to the tank circuit 606 in a first configuration in the example of FIG. 5. Other configurations are discussed below with reference to other figures. In this example, a first input of the receiver 412 is connected to the tap node 632 while a second input of the receiver 412 is connected to the high voltage node 608.

A tank switch 520 may be included between the capacitor side node 626 and the inductor side node 628. This tank switch 520 when closed can effectively bypass the rectifier during the downlink telemetry. Other options for downlink telemetry where the tank switch 520 is left open or omitted are discussed below in relation to other figures.

This embodiment of the IMD 108 is also capable of telemetry uplink by using the tank circuit 601, particularly the first portion 602 of the coil 606, and one of various methods. For instance, as shown, an H-bridge may be provided in relation to the tank circuit 601 by connecting a capacitor high side switch 530 between the load node 408 and the capacitor side node 626 while also connecting an inductor high side switch 532 between the load node 408 and the tap node 632. To prevent current from also flowing through the second portion 604 of the coil 606, a second inductor high side switch 533 may be included and the controller 302 may also employ the inductor low side switch 525. During uplink, the inductor high side switch 532 and the second inductor high side switch 533 are opened and closed at the same time while the inductor low side switch 525 and the second inductor low side switch 524 are also opened and close at the same time.

The various modes of operation of the configuration 500 operate as follows. During recharge mode when using full wave rectification, the processor/controller 302 allows all switches to remain open. As a result, the current of the tank circuit 601 including both portions 602, 604 of the coil 606 passes through the rectifier and on to the limiter 552 and ultimately to the battery 402 (as shown in FIG. 4 in connection with the recharge node 410). If half wave rectification is desired, then either capacitor low side switch 522 or inductor low side switch 525 is closed.

During recharge, one concern is that in an overcharge condition, the limiter 552 increases impedance which pumps up voltage on the rectifier recharge node 650 to a Schottky drop below the peak voltage on the capacitor side node 626 and inductor side node 628. The peak voltage on these two nodes is set by the Zener diodes 544, 546. If a large amount of energy continues to be coupled into the coil 606, then the Zener diodes 544, 546 may be subjected to significant heating which can be problematic.

In such a case, the processor/controller 302 may detect such heating or overcharge via a temperature sensor 570 or other measurement device and respond in various ways. For instance, the processor/controller 302 may change the state of the inductor low side switch 524 so that the coupling coefficient between the coil 606 and the coil of the external device 102 is decreased, thereby decreasing the power being received. Additionally or alternatively, the processor/controller 302 may close the capacitor low side switch 522 and the inductor low side switch 525 to clamp the tank circuit 601 to ground, as the coil 606, capacitors 506, and Zener diodes 514, 516 together may be better suited to dissipate the heat as part of the larger system.

During telemetry downlink, the processor/controller 302 of this example closes the inductor low side switch 524 so that the proper inductance for setting the resonant frequency of the tank circuit 601 to the telemetry frequency is achieved. The tank switch 520 is then closed. All other switches are left open, and the capacitor side node 626 is allowed to float within a diode drop below ground and above rectifier recharge node 650, respectively. The receiver 412 picks up the differential voltage across the first portion 602 of the coil 606. Several other methods of telemetry downlink are discussed below with reference to other circuit diagrams.

During telemetry uplink, the H-bridge may be operated by opening the capacitor high side switch 530 and the inductor low side switches 524 and 525 while the inductor high side switches 532 and 533 and the capacitor low side switch 522 are closed. After a set amount of time defined by the telemetry frequency, the inductor high side switches 532 and 533 and the capacitor low side switch 522 are opened while the capacitor high side switch 530 and the inductor low side switches 524 and 525 are closed. These pairings continue to alternate states to ring up the first portion 602 of the coil 606 and allow it to emit for a set amount of time. The capacitor low side switch 522 and the inductor low side switches 524 and 525 are then closed to ring down the first portion 602 of the coil 606, which remains off for a set period until time to again ring up the first portion 602 of the coil 606. In this manner, a carrier on/off protocol can be effectively implemented to uplink data. As an alternative, the first portion 602 of the coil 606 may be allowed to ring down by closing the tank switch 520 or by opening all switches and allowing the tank 601 to ring down at its natural frequency.

Figure 19:
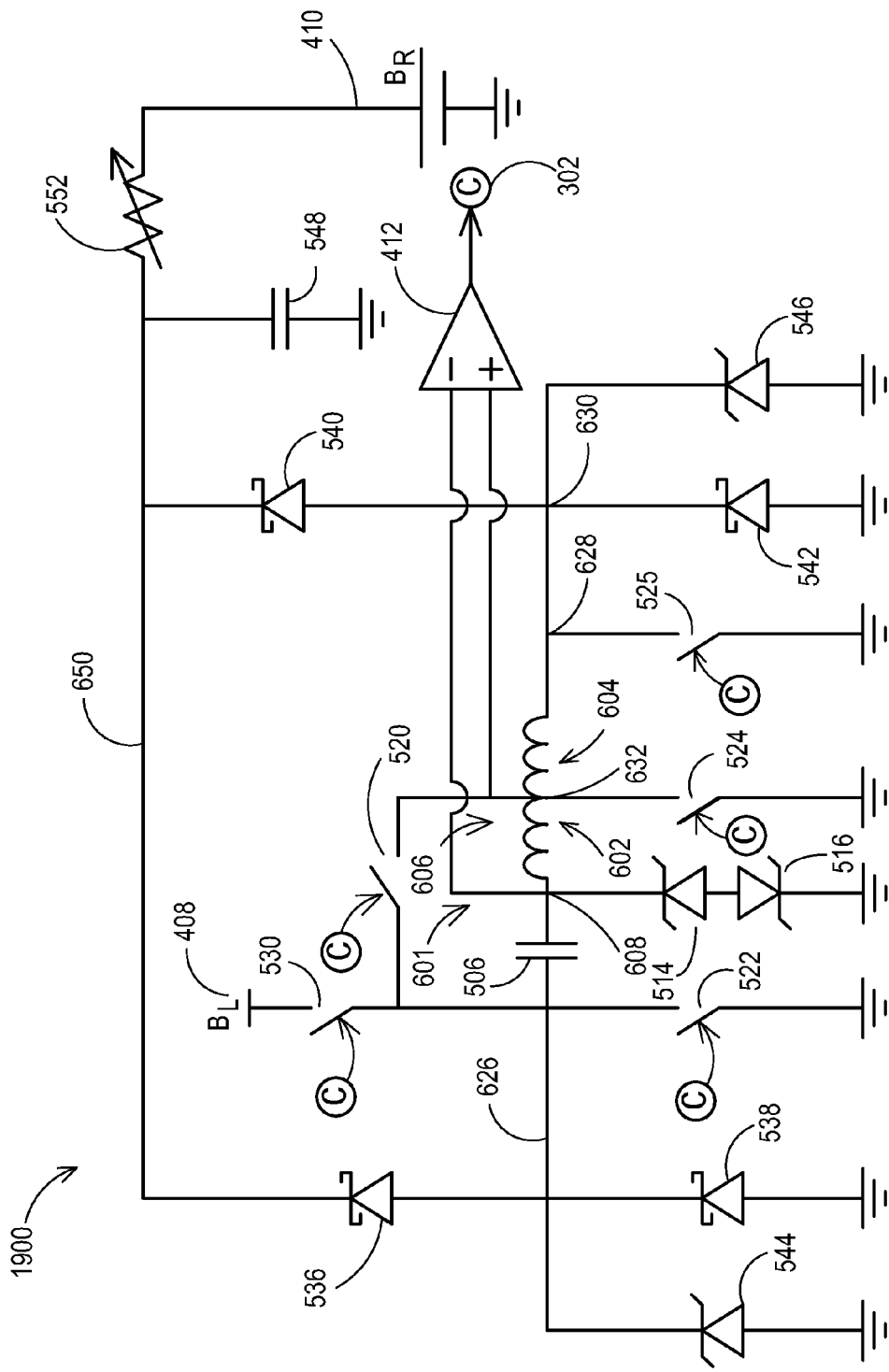
FIG. 19 shows a circuit of one example of an IMD that provides for telemetry uplink and telemetry downlink at one frequency and recharge at another frequency with multiple coil portions, with a first receiver configuration, a first rectifier configuration, and an alternative uplink switch configuration.

FIG. 19 shows another configuration 1900 that is the same as the configuration 1800 of FIG. 18 except that the H-bridge drive circuit of FIG. 18 is now a half-wave drive by removal of the inductor high side switches 532 and 533 and by alternately closing the capacitor high side switch 530 and the capacitor low side switch 522 while keeping the inductor low side switches 524 and 525 closed. This may be beneficial where it is inconvenient to have high side switches on the inductor side node 628.

Figure 20:
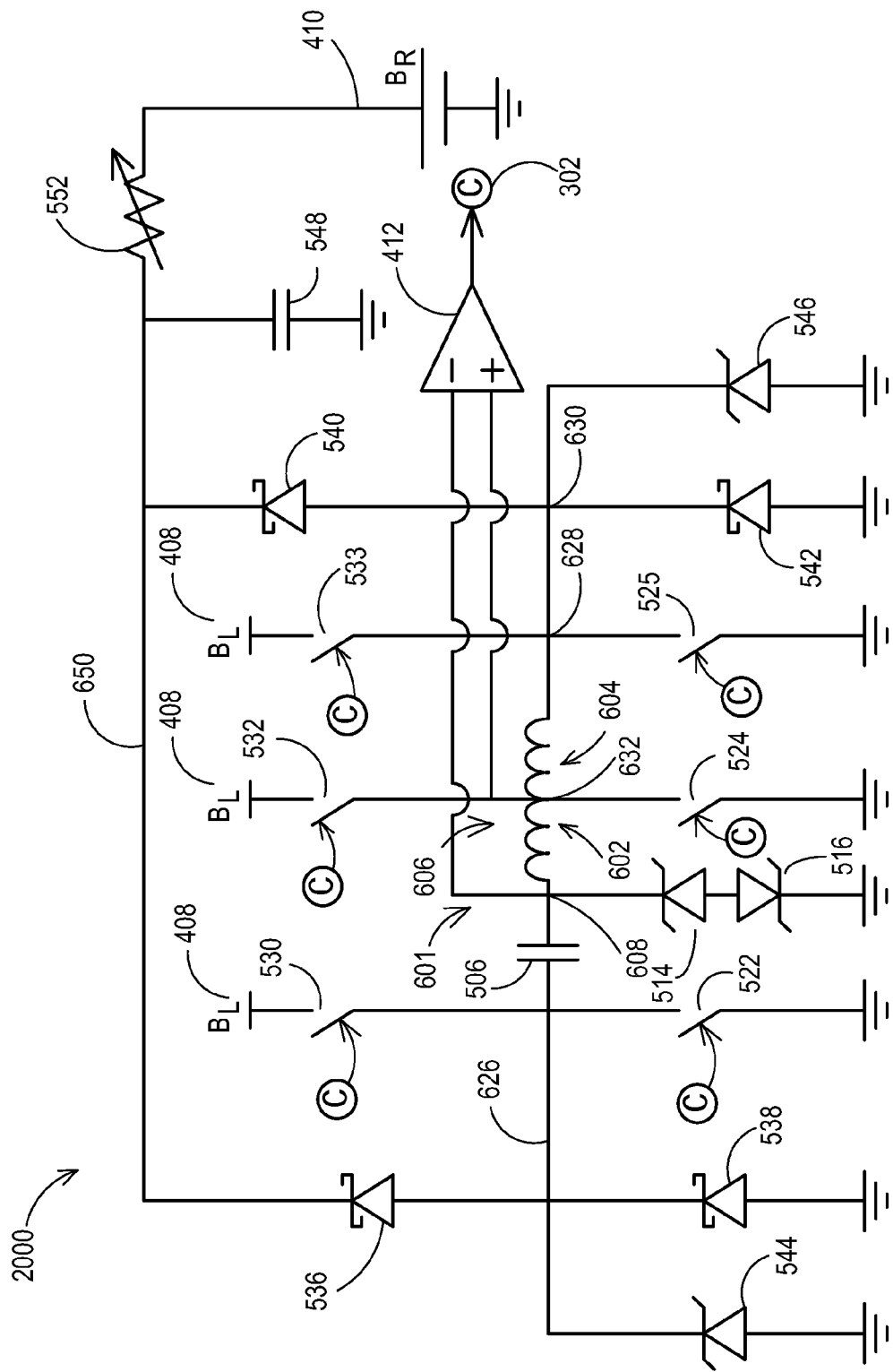
FIG. 20 shows a circuit of one example of an IMD that provides for telemetry uplink and telemetry downlink at one frequency and recharge at another frequency with multiple coil portions, with a first receiver configuration, a first rectifier configuration, and an alternative downlink switch configuration.

FIG. 20 shows another configuration 2000 that is the same as the configuration 1800 of FIG. 18 except that the tank switch 520 mentioned above is omitted. To ring down the second tank circuit 417 during uplink or to allow current to flow through the tank circuit 417 during downlink, the capacitor low side switch 522 and the inductor low side switches 524 and 525 may be closed rather than closing the tank switch 520.

Figure 21:
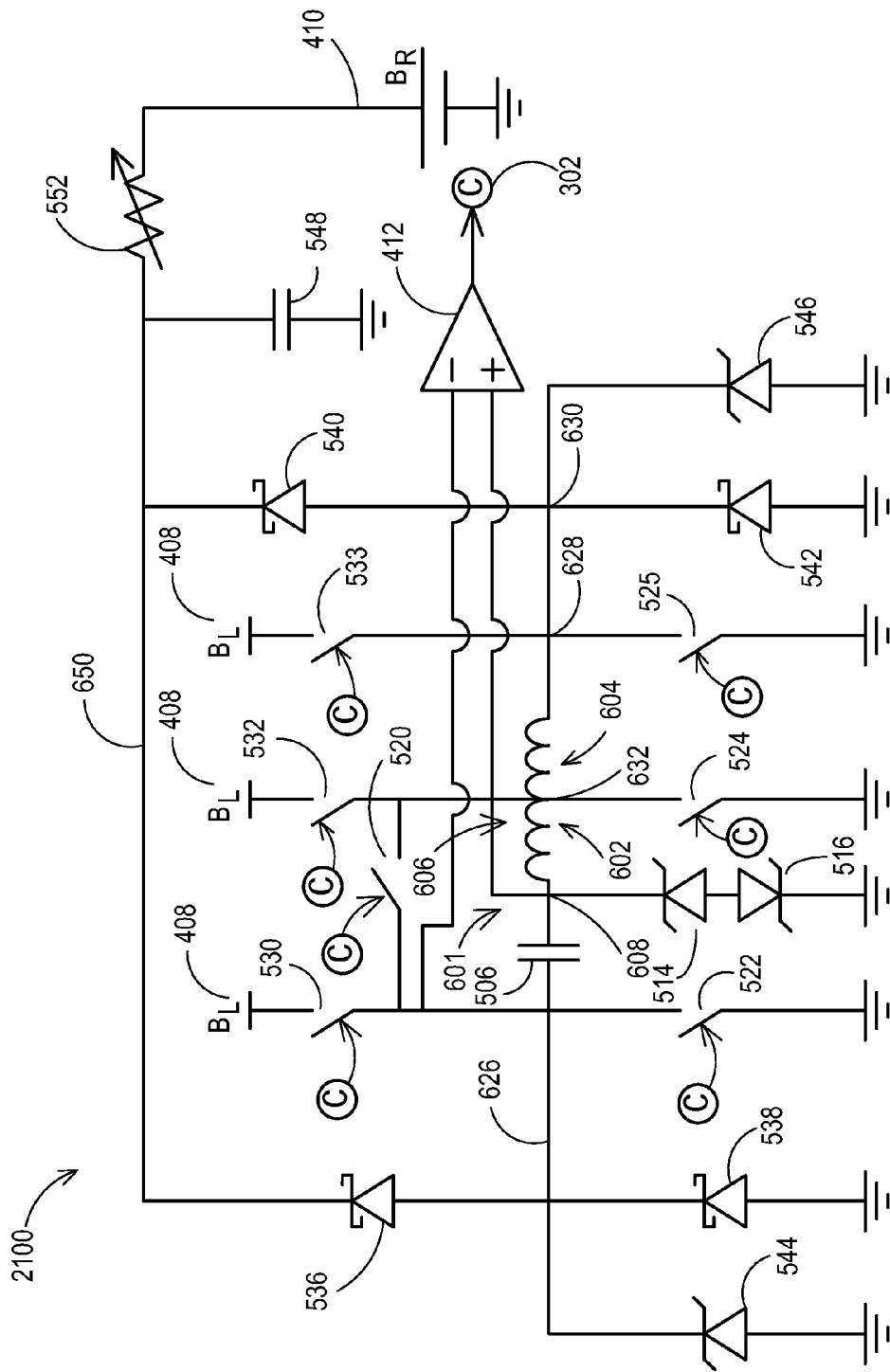
FIG. 21 shows a circuit of one example of an IMD that provides for telemetry uplink and telemetry downlink at one frequency and recharge at another frequency with multiple coil portions, with a second receiver configuration, and a first rectifier configuration.

FIG. 21 shows another configuration 2100 that is the same as the configuration 1800 of FIG. 18 except that the receiver's connectivity is configured differently. In this example, a receiver input is coupled directly to the high voltage node 608 while the other input of the receiver 412 is connected to the capacitor side node 626 rather than the tap node 632. The capacitor low side switch 522 and the inductor low side switches 524 and 525 may be closed when receiving telemetry. All other switches are open when receiving telemetry signals except the tank switch 520 may be closed when present.

Figure 22:
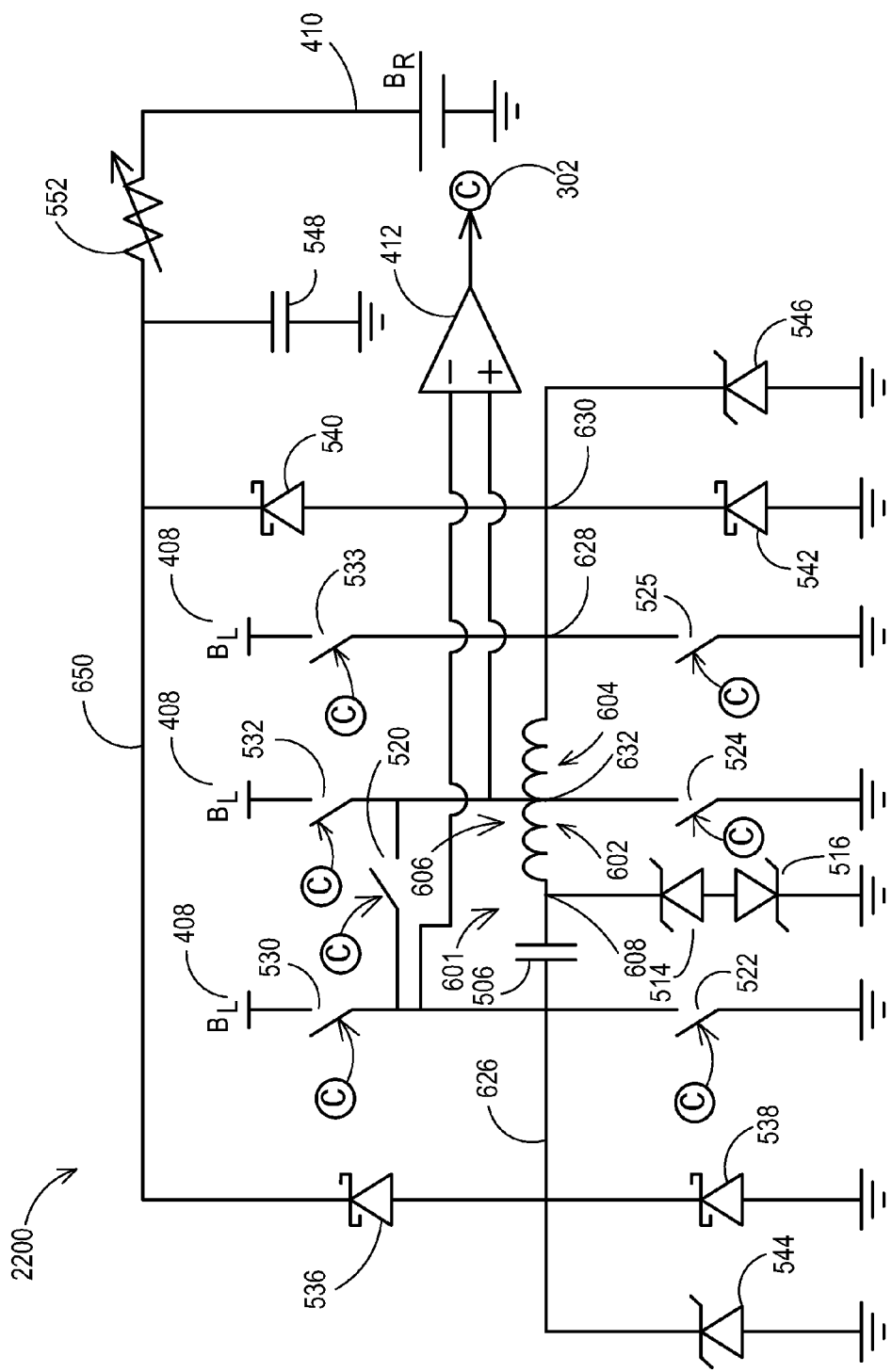
FIG. 22 shows a circuit of one example of an IMD that provides for telemetry uplink and telemetry downlink at one frequency and recharge at another frequency with multiple coil portions, with a third receiver configuration, and a first rectifier configuration.

FIG. 22 shows another configuration 2200 that is the same as the configuration 1800 of FIG. 18 except that the receiver's connectivity is configured differently. Here, the receiver 412 is connected differentially across the active portion of the tank circuit 601 by having a receiver input coupled directly to the tap node 632 while another receiver input is coupled directly to the capacitor side node 626. The capacitor low side switch 522 and the inductor low side switches 524 and 525 may be closed when receiving telemetry. All other switches are open when receiving telemetry signals except the tank switch 520 may be closed when present.

Figure 23:
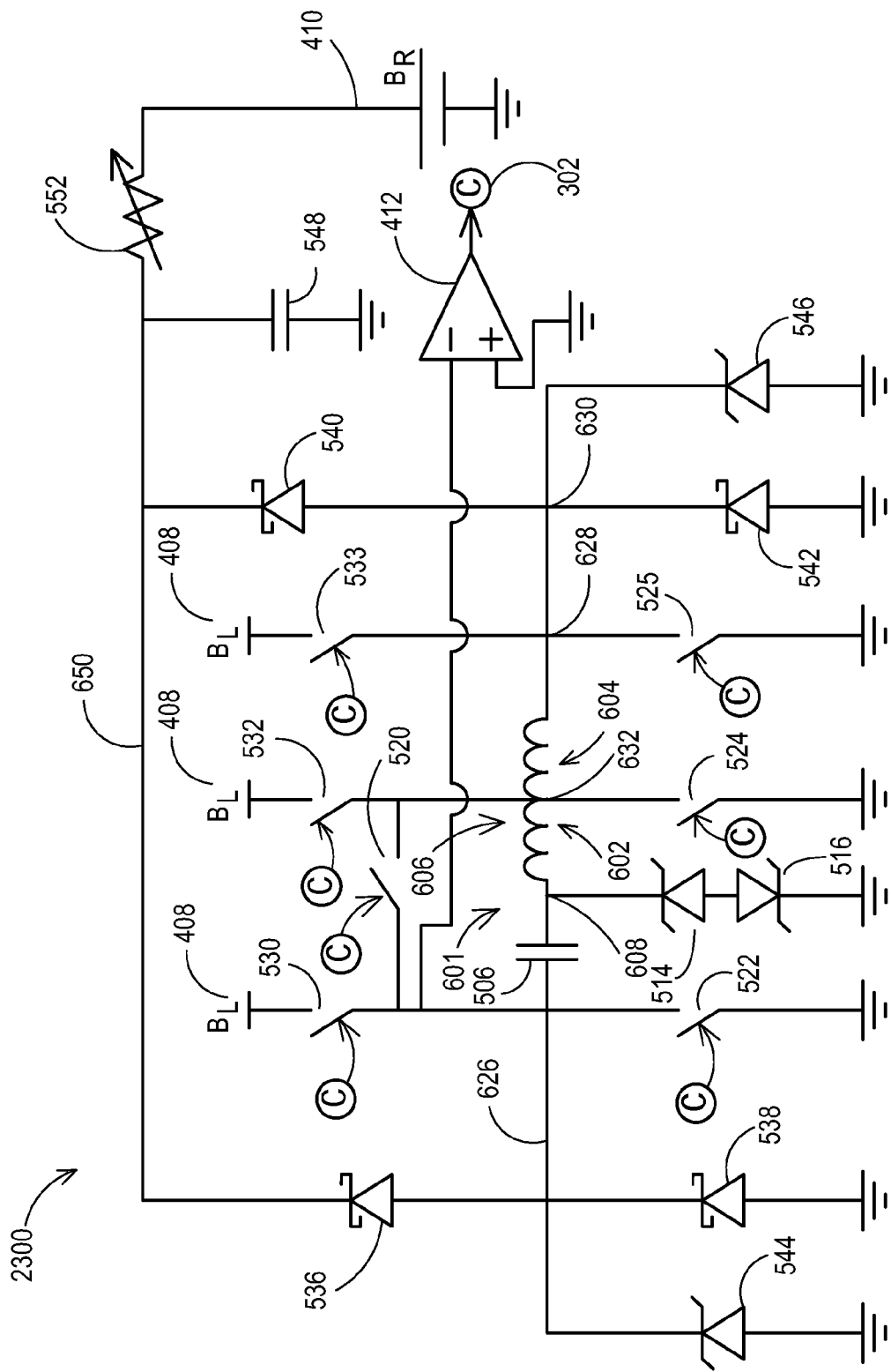
FIG. 23 shows a circuit of one example of an IMD that provides for telemetry uplink and telemetry downlink at one frequency and recharge at another frequency with multiple coil portions, with a fourth receiver configuration, and a first rectifier configuration.

FIG. 23 shows another configuration 2300 that is the same as the configuration 1800 of FIG. 18 except that the receiver's connectivity is configured differently. Here, one input of the receiver 412 is connected to the capacitor side node 626 while the other input of the receiver 412 is connected to ground. The capacitor low side switch 522 and the inductor low side switches 524 and 525 may be closed when receiving telemetry. All other switches are open when receiving telemetry signals except the tank switch 520 may be closed when present.

Figure 24:
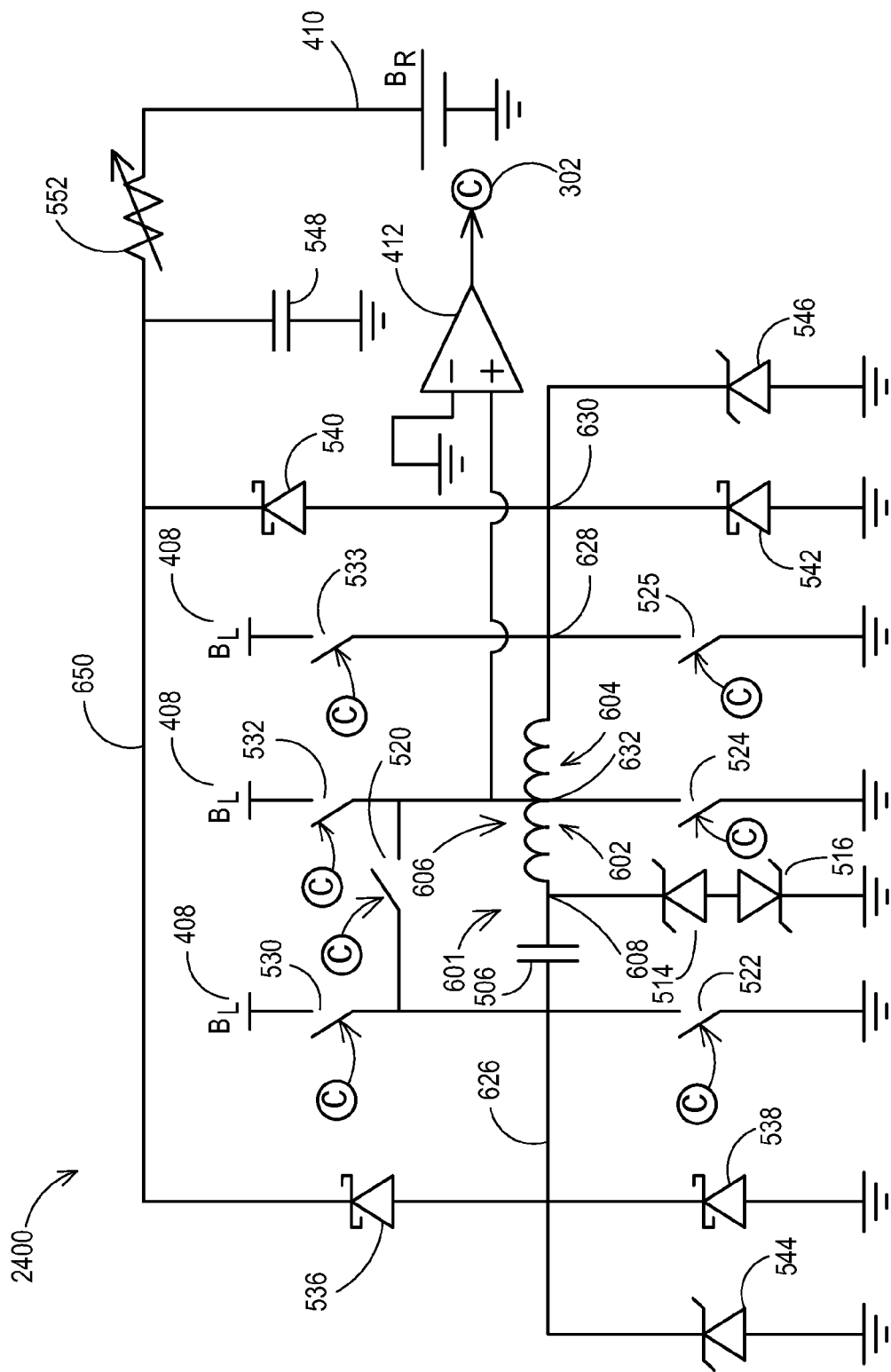
FIG. 24 shows a circuit of one example of an IMD that provides for telemetry uplink and telemetry downlink at one frequency and recharge at another frequency with multiple coil portions, with a fifth receiver configuration, and a first rectifier configuration.

FIG. 24 shows another configuration 2400 that is the same as the configuration 1800 of FIG. 18 except that the receiver's connectivity is configured differently. Here, one input of the receiver 412 remains connected to the tap node 632 while the other input of the receiver 412 is connected to ground. The capacitor low side switch 522 and the inductor low side switches 524 and 525 may be closed when receiving telemetry. All other switches are open when receiving telemetry signals except the tank switch 520 may be closed when present.

Figure 25:
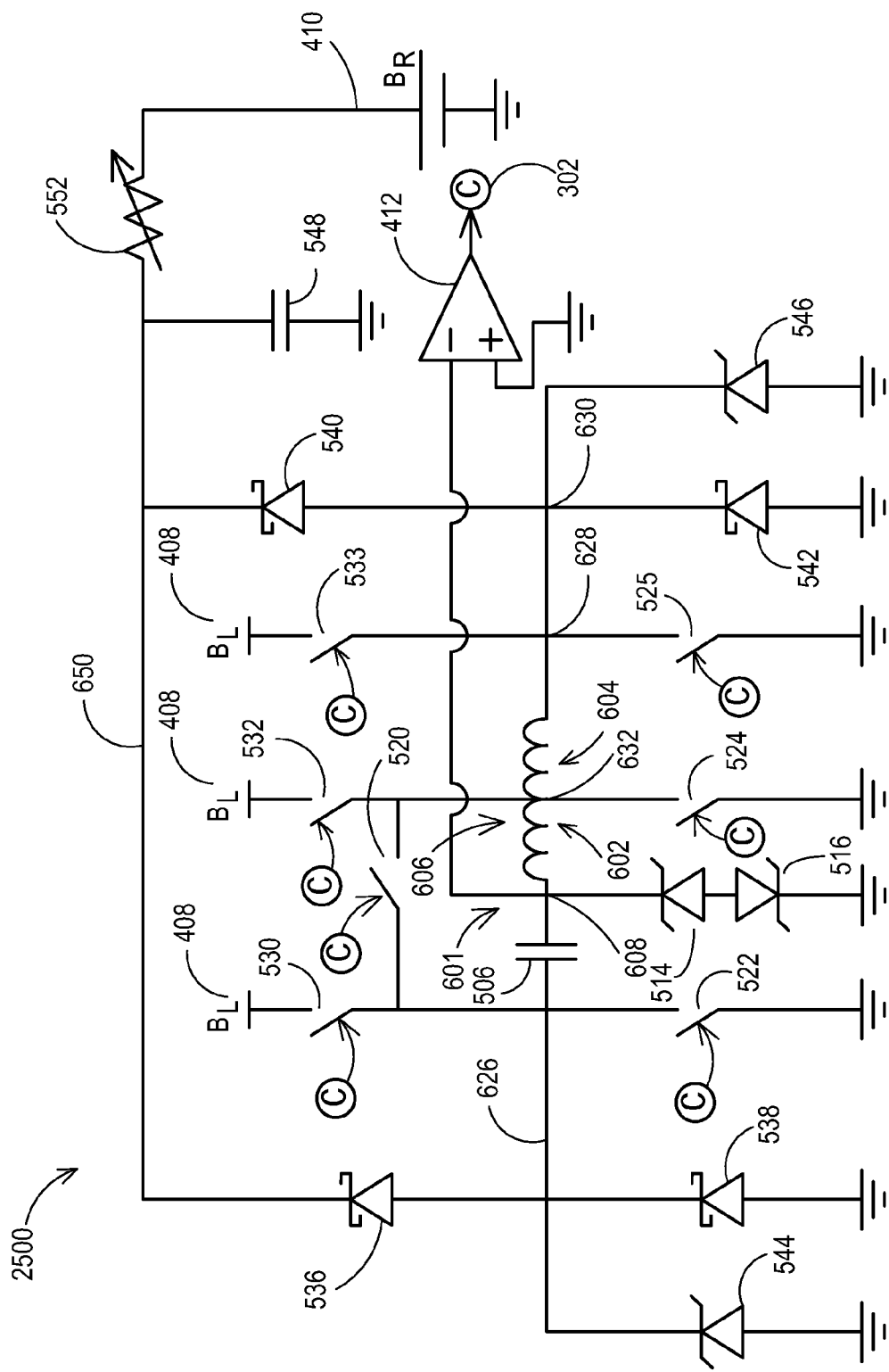
FIG. 25 shows a circuit of one example of an IMD that provides for telemetry uplink and telemetry downlink at one frequency and recharge at another frequency with multiple coil portions, with a sixth receiver configuration, and a first rectifier configuration.

FIG. 25 shows another configuration 2500 that is the same as the configuration 1800 of FIG. 18 except that the receiver's connectivity is configured differently. Here, one input of the receiver 412 is connected directly to the high voltage node 608 while the other input of the receiver 412 is connected to ground. The capacitor low side switch 522 and the inductor low side switches 524 and 525 may be closed when receiving telemetry. All other switches are open when receiving telemetry signals except the tank switch 520 may be closed when present.

Figure 26:
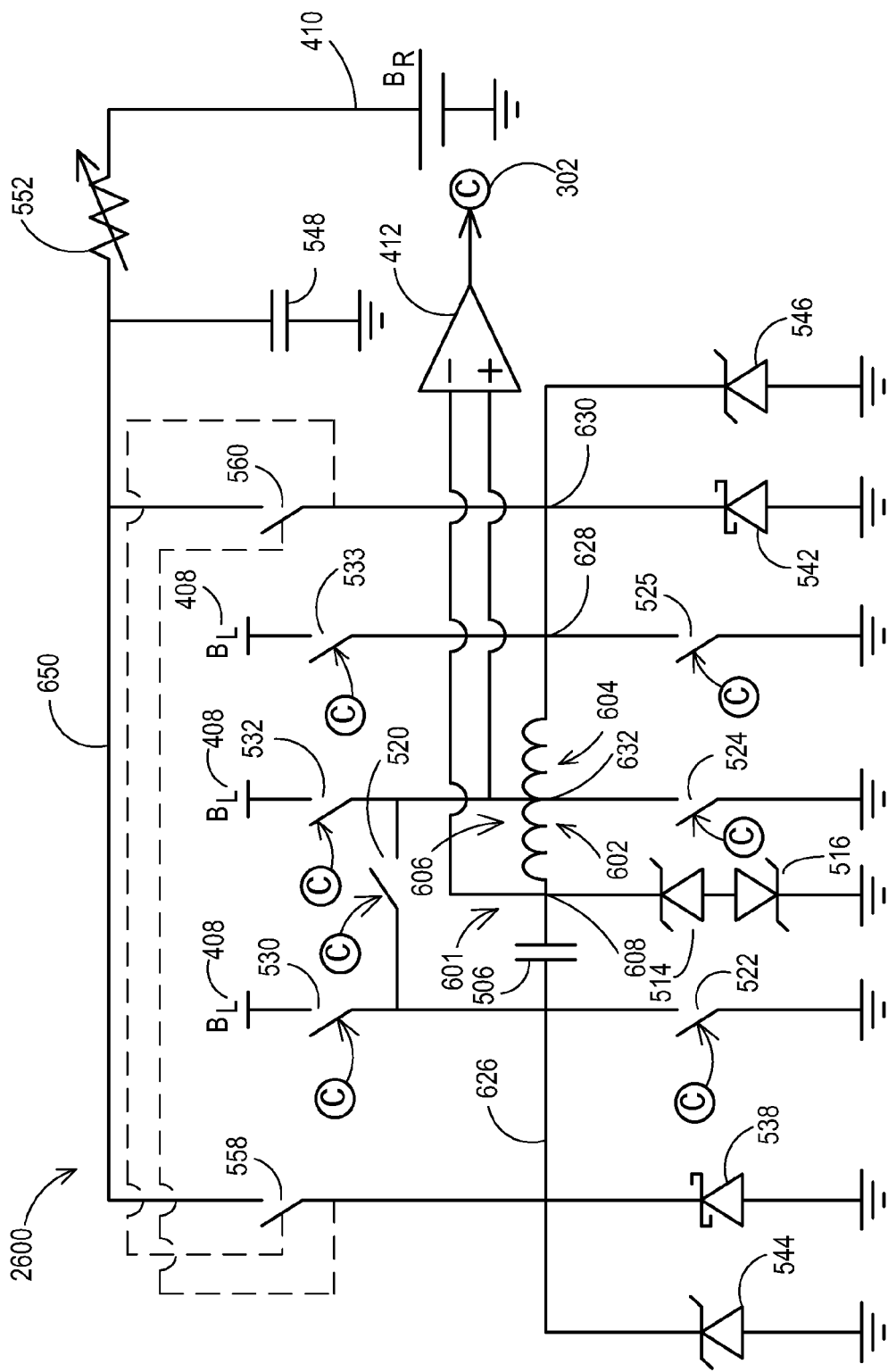
FIG. 26 shows a circuit of one example of an IMD that provides for telemetry uplink and telemetry downlink at one frequency and recharge at another frequency with multiple coil portions, with a first receiver configuration, and a second rectifier configuration.

FIG. 26 shows a configuration 2600 that is the same as the configuration 1800 of FIG. 18 except that the rectifier is different. In this configuration 2600, the rectifier may use both high side and low side synchronous rectification by including a capacitor high side rectifier switch 558 and an inductor high side rectifier switch 560 in place of high side diodes. As discussed for the configuration of FIG. 18, the capacitor low side switch 522 and the inductor low side switch 525 may operate to provide the low side synchronous rectification.

In this particular example, the low side synchronous rectifier switches 522, 525 may be N-MOS devices while the high side synchronous rectifier switches 558, 560 may be P-MOS devices. The result based on the state machine control by the processor/controller 302 is that when the inductor side flies high, the inductor high side switch 560 and the capacitor low side switch 522 are closed while the capacitor high side switch 558 and the inductor low side switch 525 are open. When the capacitor side flies high, the capacitor high side switch 558 and the inductor low side switch 525 are closed while the inductor high side switch 560 and the capacitor low side switch are open.

The synchronous rectifier of FIG. 26 may be a pure full wave synchronous rectifier as another alternative. In that case, the diodes 538 and 542 are omitted.

While this operation of the switches 522, 525, 558, and 560 applies to recharge, during uplink and downlink telemetry operations, the capacitor low side switch 522 and the inductor low side switch 525 may operate in the same manner as discussed above in relation to FIG. 18. The capacitor high side switch 558 and the inductor high side switch 560 may remain open during uplink and downlink telemetry operations.

Figure 27:
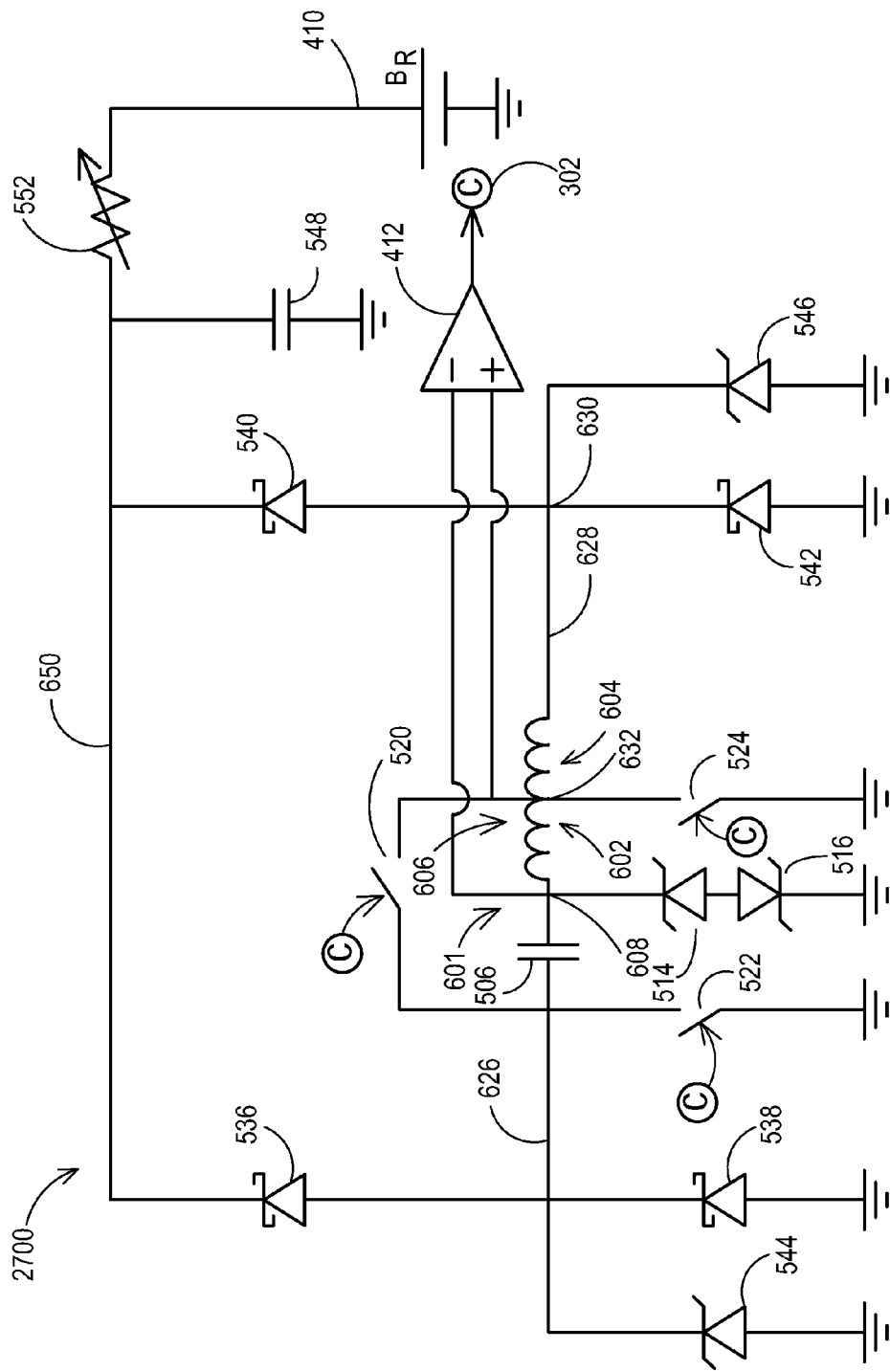
FIG. 27 shows a circuit of one example of an IMD that provides for telemetry downlink at one frequency and recharge at another frequency with multiple coil portions, with a first receiver configuration, and a first rectifier configuration.

FIG. 27 shows another configuration 2700 like the configuration 1800 of FIG. 18, except that the high side of the H-bridge created by the capacitor high side switch 530 and inductor high side switch 532 has been omitted. In this situation, the coil 601 is being used for recharge and downlink telemetry. Uplink telemetry may be unnecessary in some contexts for an IMD 108. As another example, uplink telemetry may be provided at a separate frequency than downlink telemetry and may utilize a separate circuit and coil from that shown so that full-duplex communication with the external device 102 may be achieved. The variations discussed above in FIGS. 18-26 and below in FIG. 33 are also applicable to the configuration 2700 to the extent those variations relate to recharging, telemetry downlink, and power management.

Figure 28:
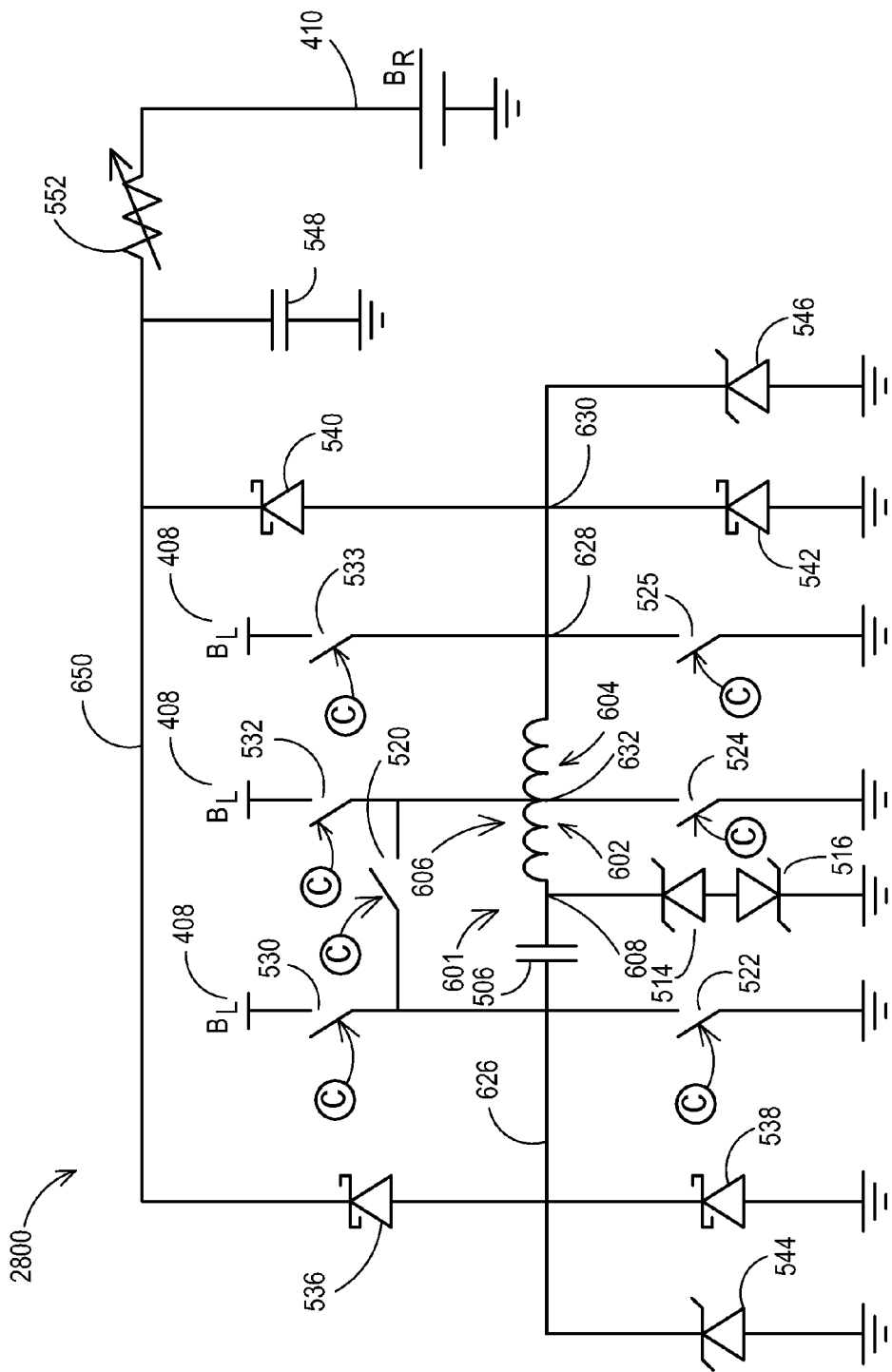
FIG. 28 shows a circuit of one example of an IMD that provides for telemetry uplink at one frequency and recharge at another frequency with multiple coil portions and a first rectifier configuration.

FIG. 28 shows another configuration 2800 like the configuration 1800 of FIG. 18, except that the receiver 412 has been omitted. In this situation, the coil 601 is being used for recharge and uplink telemetry. Downlink telemetry may be unnecessary in some contexts for an IMD 108. As another example, downlink telemetry may be provided at a separate frequency than uplink telemetry and may utilize a separate circuit and coil from that shown so that full-duplex communication with the external device 102 may be achieved. The variations discussed above in FIGS. 18-26 and below in relation to FIG. 33 are also applicable to the configuration 2800 to the extent those variations relate to recharging, telemetry uplink, and power management.

Figure 29:
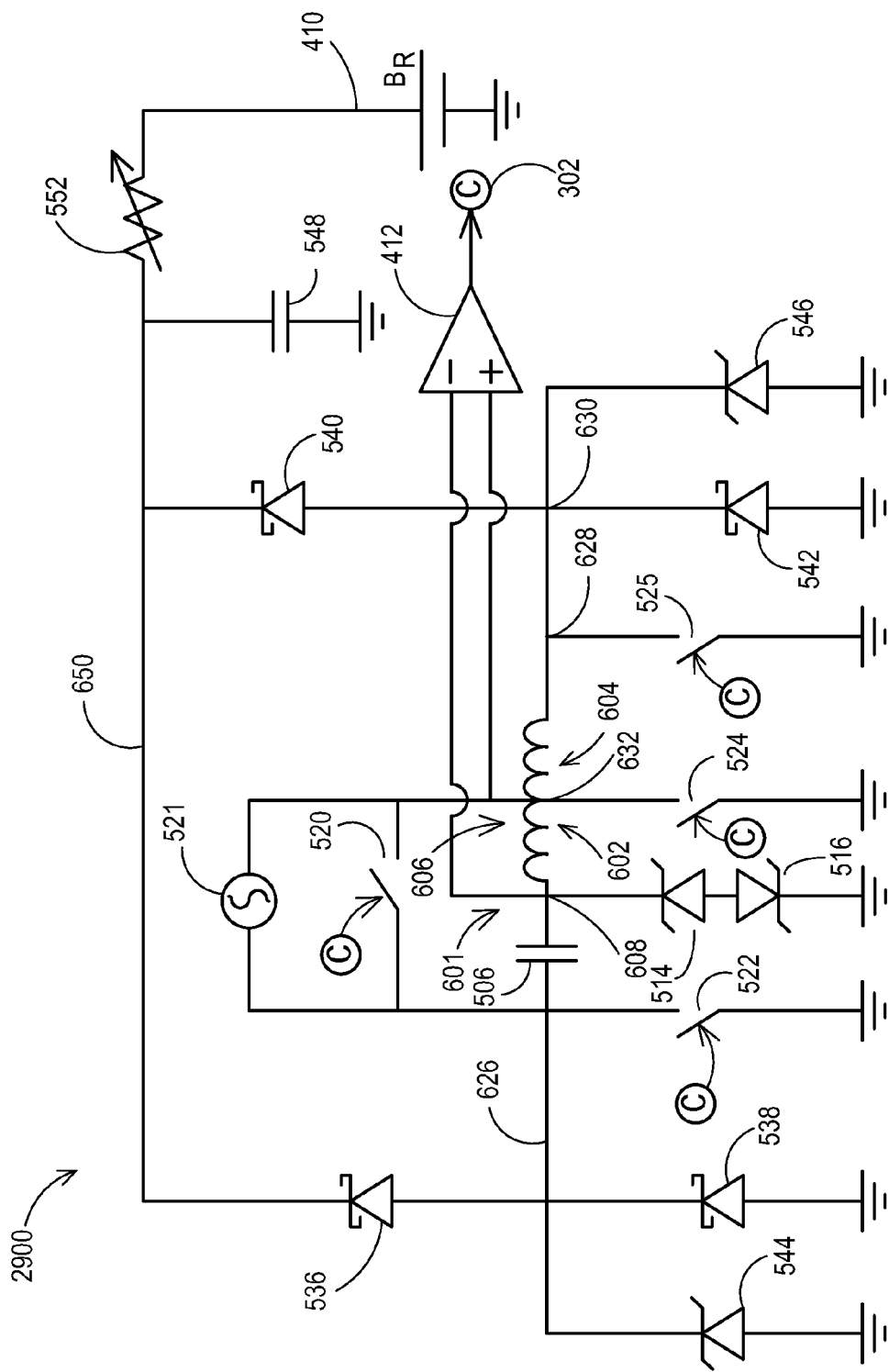
FIG. 29 shows a circuit of one example of an IMD that provides for telemetry uplink and telemetry downlink at one frequency and recharge at another frequency with multiple coil portions, a first receiver configuration, a first rectifier configuration, and with an oscillator for uplink.

FIG. 29 shows another configuration 2900 like the configuration 1800 of FIG. 18 except that the transmission switches 522, 524, 525, 530, 532, and 533 are no longer being used to ring the coil 601. Instead, an oscillator 521 such as a sinusoidal power amplifier is connected across the tank circuit 601, particularly across the first portion 602 of the coil 606, to drive the tank circuit 601 at the uplink frequency. The oscillator 521 may be activated and deactivated by the controller 302 which may also switch the oscillator 521 into and out of the circuit. This oscillator 521 may result in fewer harmonics on the uplink carrier. It will be appreciated that all of the variations discussed above in FIGS. 18-26 and 28 are also applicable to the example of FIG. 29.

Figure 33:
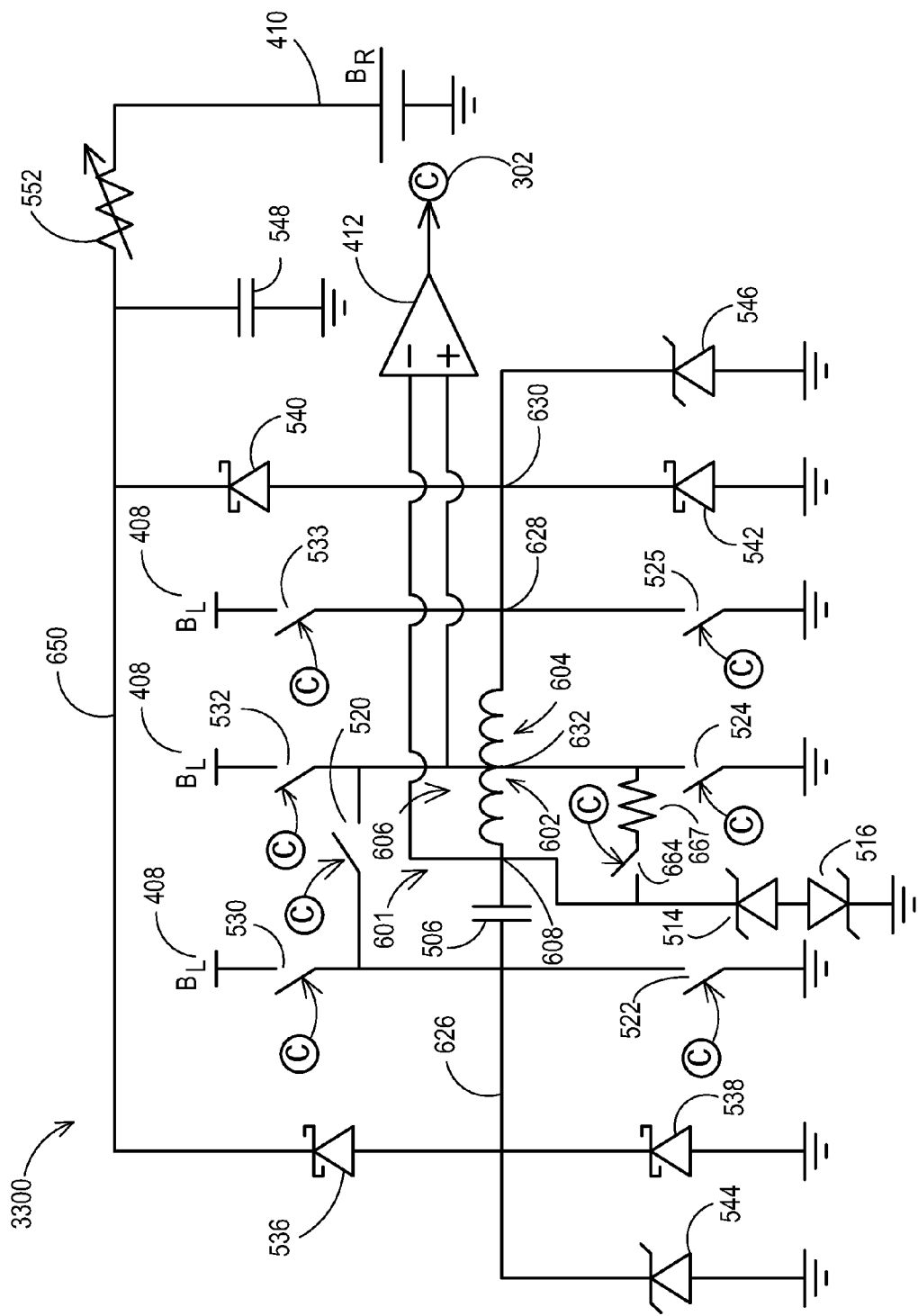
FIG. 33 shows a circuit of one example of an IMD that provides for telemetry uplink and telemetry downlink at one frequency and recharge at another frequency with multiple coil portions, a first receiver configuration, a first rectifier configuration, and including a snubbing resistor for power management and/or telemetry uplink.

FIG. 33 shows a configuration 3300 which is identical to the configuration 1800 of FIG. 18 except that a circuit pathway is provided that includes a snubbing resistor 667 and a snubbing switch 664 that is under control of the processor/controller 302 in parallel with the first portion 602 of the coil 601. This circuit pathway provides power management in the event of an overcharge condition in addition to or as an alternative to the power management methods discussed above for FIG. 18. Because the snubbing switch 664 may be closed to allow some tank circuit current to pass through the snubbing resistor 667 to dissipate the energy as heat in that component and to lower the Q of the tank circuit 601, there is less energy to be dissipated by the Zener devices 544, 546 and 514, 516.

This circuit pathway including the snubbing switch 664 and snubbing resistor 667 may have other uses as well. For instance, the telemetry of the external device 102 may be configured to receive information by monitoring for a change in the mutual inductance between the coil of the external device 102 and the coil 601 of the IMD 108 that is caused by the IMD 108 while the external device 102 is emitting a signal. This change in the mutual inductance by the IMD 108 can be viewed as a transmission of information, for example where an on-off fashion of the change in mutual inductance is similar to a carrier on-off protocol. In such a case, the H-bridge may be unnecessary and the capacitor high side switch 530 and inductor high side switches 532 and 533 may be omitted, although low side switches 522, 524, and 525 may be retained for other purposes such as to ground the tank circuit 601.

The circuit pathway including the snubbing switch 664 and the snubbing resistor 667 is shown in the configuration 3300 of FIG. 33 as a modification to the configuration 1800 of FIG. 18. However, it will be appreciated that this circuit pathway may be included as a modification to other configurations as well, including those discussed below in relation to FIGS. 19-29.

While embodiments have been particularly shown and described, it will be understood by those skilled in the art that various other changes in the form and details may be made therein without departing from the spirit and scope of the invention.

The invention claimed is:

1. An implantable medical device, comprising:
   a first tank circuit that is tuned to a first frequency and that comprises a first coil portion and a separate first capacitance electrically connected in a series combination directly with the first coil portion;
   a second tank circuit that is tuned to a second frequency that is different than the first frequency and the second tank circuit further comprising a second coil portion and a separate second capacitance electrically connected in a series combination directly with the second coil portion, the series combination of the second coil portion and the second capacitance being directly electrically connected to the series combination of the first coil portion and the first capacitance with a connection point between the first tank circuit and the second tank circuit establishing a first node;
   a receiver with at least one input that is electrically connected directly to the second coil portion or the second capacitance and not directly electrically connected to the first coil portion and the first capacitance;
   a battery;
   a rectifier electrically coupled between the battery and across at least one of the first coil portion and the first capacitance of the first tank circuit;
   and
   medical circuitry electrically coupled to the battery.

2. The implantable medical device of claim 1, wherein the first coil portion and the second coil portion are geometrically oriented so that current of the first tank circuit sums with current of the second tank circuit at the first node.

3. The implantable medical device of claim 1, wherein the receiver is connected across the second coil portion.

4. The implantable medical device of claim 1, wherein the rectifier is a full-wave rectifier.

5. The implantable medical device of claim 4, wherein the first tank circuit comprises a second node on a side of the first tank circuit opposite the first node, wherein the rectifier comprises a first pair of diodes where a first diode of the first pair is electrically connected between the first node of the first tank circuit and ground and a second diode of the first pair is electrically connected between the second node of the first tank circuit and the battery allowing current flowing through the first tank circuit in a first direction to be directed to the battery and a second pair of diodes where a first diode of the second pair is electrically connected between the second node of the first tank circuit and ground and a second diode of the second pair is electrically connected between the first node of the first tank circuit and the battery allowing current flowing through the first tank circuit in a second direction to be directed to the battery.

6. The implantable medical device of claim 1, further comprising a switch electrically coupled between one side of the rectifier and ground, and a controller setting the switch to an open state to provide full wave rectification and setting the switch to a closed state to provide half wave rectification.

7. The implantable medical device of claim 1, further comprising a recharge limiter in series with the battery.

8. The implantable medical device of claim 7, further comprising a filter capacitor in parallel with the recharge limiter and battery.

9. The implantable medical device of claim 1, further comprising a capacitor low side switch coupled between the second capacitance and ground and an inductor low side switch coupled between the second coil portion and ground.

10. The implantable medical device of claim 9, wherein the second tank circuit comprises a node shared by the capacitor low side switch and the second capacitance and a node shared by the inductor low side switch and the second coil portion, wherein the at least one input of the receiver comprises a first input and a second input, wherein the first input of the receiver is connected to the node shared by the capacitor low side switch and second capacitance or to the node shared by the inductor low side switch and second coil portion and wherein the second input of the receiver is connected to the node of the second tank circuit other than the node connected to the first input.

11. The implantable medical device of claim 1, further comprising:
   drive circuitry coupled to opposite sides of the second tank circuit; and
   a controller in electrical communication with the drive circuitry, the controller comprising logic to control the drive circuitry to ring the second tank circuit when sending telemetry signals and to not ring the second tank circuit when receiving recharge energy on the first tank circuit.

12. A medical system, comprising:
   an external device comprising:
     a telemetry module;
     a controller that sends telemetry signals through the telemetry module; and
   an implantable medical device comprising:
     a first tank circuit that is tuned to a first frequency and that comprises a first coil portion and a separate first capacitance electrically connected in a series combination directly with the first coil portion;
     a second tank circuit that is tuned to a second frequency that is different than the first frequency and the second tank circuit further comprising a second coil portion and a separate second capacitance electrically connected in a series combination directly with the second coil portion, the series combination of the second coil portion and the second capacitance being directly electrically connected to the series combination of the first coil portion and the first capacitance with a connection point between the first tank circuit and the second tank circuit establishing a first node;
     a receiver with at least one input that is electrically connected directly to the second coil portion or the second capacitance and not directly electrically connected to the first coil portion and the first capacitance;
     a battery;
     a rectifier electrically coupled between the battery and across at least one of the first coil portion and the first capacitance of the first tank circuit; and
     medical circuitry electrically coupled to the battery.

13. The medical system of claim 12, wherein the first coil portion and the second coil portion are geometrically oriented so that current of the first tank circuit sums with current of the second tank circuit at the first node.

14. The medical system of claim 12, wherein the receiver is connected across the second coil portion.

15. The medical system of claim 12, further comprising a switch electrically coupled between one side of the rectifier and ground, and a device controller setting the switch to an open state to provide full wave rectification and setting the switch to a closed state to provide half wave rectification.

16. A method of providing telemetry and recharging for an implantable medical device, comprising:
   receiving a first collection of energy at a first frequency via a first tank circuit of an implantable medical device that is tuned to the first frequency by a first coil portion and a separate first capacitance of the first tank circuit that are directly electrically connected in a series combination;

receiving a second collection of energy at a second frequency via a second tank circuit of the implantable medical device that is tuned to the second frequency by a second coil portion and a separate second capacitance of the second tank circuit that are directly electrically connected in a series combination;

obtaining the second collection of energy from the second tank circuit at a receiver of the implantable medical device, the receiver comprising at least one input that is directly connected to the second coil portion or the second capacitance and not directly electrically connected to the first coil portion and the first capacitance passing the first collection of energy from the first tank circuit through a rectifier of the implantable medical device that is electrically coupled across at least one of the first coil portion and the first capacitance of the first tank circuit to provide a rectified collection of energy to a battery of the implantable medical device, the battery being electrically coupled to the rectifier; and providing the rectified collection of energy from the battery to medical circuitry of the implantable medical device, the medical circuitry being electrically coupled to the battery.

17. The method of claim 16, wherein the first coil portion and the second coil portion are geometrically oriented so that current of the first tank circuit sums with current of the second tank circuit at the first node.

18. The method of claim 16, wherein the receiver is connected across the second coil portion.

19. The method of claim 16, wherein the implantable medical device has a switch electrically coupled between one side of the rectifier and ground, and the method further comprising setting the switch to an open state to provide full wave rectification and setting the switch to a closed state to provide half wave rectification.

20. An implantable medical device, comprising:
a first tank circuit that is tuned to a first frequency and that comprises a first coil portion and a separate first capacitance electrically connected in a series combination with the first coil portion, the series combination of the first coil portion and the first capacitance being electrically connected to a first node;
a second tank circuit that is tuned to a second frequency that is different than the first frequency and the second tank circuit further comprising a second coil portion and a separate second capacitance electrically connected in a series combination with the second coil portion, the series combination of the second coil portion and the second capacitance being electrically connected to the first node;
a receiver with at least one input electrically connected to the second tank circuit;
a battery;
a rectifier electrically coupled between the battery and the first tank circuit; and
medical circuitry electrically coupled to the battery,
wherein the rectifier is a full-wave rectifier, wherein the first tank circuit comprises a second node on a side of the first tank circuit opposite the first node, wherein the rectifier comprises a first pair of diodes where a first diode of the first pair is electrically connected between the first node of the first tank circuit and ground and a second diode of the first pair is electrically connected between the second node of the first tank circuit and the battery allowing current flowing through the first tank circuit in a first direction to be directed to the battery and a second pair of diodes where a first diode of the second pair is electrically connected between the second node of the first tank circuit and ground and a second diode of the second pair is electrically connected between the first node of the first tank circuit and the battery allowing current flowing through the first tank circuit in a second direction to be directed to the battery.

* * * * *